(12) United States Patent
Bafor et al.

(10) Patent No.: US 6,333,448 B1
(45) Date of Patent: Dec. 25, 2001

(54) PLANT ENZYME AND USE THEREOF

(76) Inventors: Maureen Bafor, P.O. Box 4196, Benin City (NG); Antoni Banas, ul. Wiolinowa 14, 08-110 Siedlce (PL); Anders Dahlqvist, Hemmansvagen 2, S-244 66 Furuland (SE); Per-Olov Gummeson, Bjornbarsstigen 5, S-227 38 Lund (SE); Michael Lee, Storgatan 11, S-231 97 Klagstorp (SE); Staffan Sjodal, Valthornsvagen 22, S-756 50 Uppsala (SE); Sten Stymne, Torrlosa 1380, S-268 90 Svalov (SE); Marit Lenman, Revingegatan 13 A, S-22359 Lund (SE)

( * ) Notice: Subject to any disclaimer, the term of this patent is extended or adjusted under 35 U.S.C. 154(b) by 0 days.

(21) Appl. No.: 09/161,994

(22) Filed: Sep. 29, 1998

Related U.S. Application Data

(63) Continuation-in-part of application No. PCT/SE97/00247, filed on Feb. 14, 1997.

(30) Foreign Application Priority Data

Mar. 29, 1996 (SE) .................................................... 9601236

(51) Int. Cl.$^7$ ............................. A01H 5/00; C12N 15/82; C12N 1/14; C12N 1/16
(52) U.S. Cl. ........................ 800/295; 800/281; 536/23.6; 435/69.1; 435/254.1; 435/255.1; 435/419
(58) Field of Search .................................... 800/281, 278, 800/298, 295; 536/23.6; 435/69.1, 440, 468, 471, 325, 410, 419, 255.1, 254.1

(56) References Cited

PUBLICATIONS van de Loo et al., "An oleate 12–hydroxylase from Ricinus communis L. is a fatty acyl desaturase homolog" Proc. Natl. Acad. Sci., vol.92, pp. 6743–6747, (1995).
Wieland et al., "Genetic and Biochemical Analyses of the Biosynthesis of the Yellow Carotenoid 4, 4'–Diaponeurosporene of Staphylococcus aureus", Journal of Bacteriology, pp. 7719–7726, (1994).
Vernet et al., "A family of yeast expression vectors containing the phage f1 intergenic region", Gene, vol. 52, pp. 225–233, (1987).
Shanklin et al., "Eight Histidine Residues Are Catalytically Essential in a Membrane–Associated Iron Enzyme, Stearoyl–CoA Desaturase, and Are Conserved in Alkane Hydroxylase and Xylene Monooxygenase" American Chemical Society, vol. 33, pp. 12787–12794, (1994).
Langridge et al., "Extraction of Nucleic Acids from Agarose Gels", Analytical Biochemistry, vol. 103 pp. 264–271, (1980).

"The biosynthesis of an acetylenic acids, crepenynic acids", Biochim. Biophys. Acta, vol. 137, pp. 391–392 (1967).
Diedrich et al., "The natural occurrence of unusual fatty acids Part 3. Acetylenic fatty acids" die Nahrung 35, vol. 2, pp. 193–202, (1991).
Birnboim et al., "A rapid alkaline extraction procedure for screening recombinant plasmid DNA" Nucleic Acids Research, vol. 7, No. 6, pp. 1513–1523, (1979).
Badami et al., "Structure and Occurrence of Unusual Fatty Acids in Minor Seed Oils", Prog. Lipid Res. vol. 19, pp. 119–153, (1981).
BioFeedback, "A Simple and Efficient Procedure for Transformation of Yeast", BioTechniques, vol. 13, No. 1 pp. 18–20, (1992).
Nilsson et al., "The Determination of Double Bond Positions in Polyunsaturated Fatty Acids–Gas Chromatography/Mass Spectrometry of the Diethylamide Derivative", Phytochemical Analysis, vol. 2, pp. 253–259, (1991).
Kohn, Gerhard et al., "Biosynthesis of acetylenic fatty acids in the moss Ceratodon purpureus (Hedw.) brid." J. Plant Physio., vol. 144, pp. 265–271 (1994).
Haigh, W.G. et al., "Acetylenic acid biosynthesis in Crepis rubra.", Lipids, vol. 3, pp. 307–312 (1968).
Haigh, W.G. et al., "The biosynthesis of an acetylenic acid, crepenynic acid.", Biochim. Biophys. Acta., vol. 137, pp. 391–392 (1967).
Van de Loo et al., "Unusual Fatty Acids" In: Lipid Metabolism in Plants, (ed.) T.S. Moore, CRC Press, Boca Raton, p. 105 (1993).
Hirsinger, "New Annual Oil crops", In: Oil Crops of the World, (eds.) G. Räbbelen, R. K. Downey, and Downey, and A. Ashri, McGraw–Hill, Inc., pp. 518–532 (1989).
Banas et al., "Biosynthesis of an Acetylenic Fatty Acid in Microsomal Preparation from Developing Seeds of Crepis alpina", In: Physiology, Biochemistry and Molecular Biology of Plant Lipids, (eds.) Williams, J.P. Mobasher, K. U., Lem, N.W., Kluwer Academic Publishers, Dordrecht, pp. 57–59 (1997).

Primary Examiner—Elizabeth F. McElwain
(74) Attorney, Agent, or Firm—Browdy and Neimark

(57) ABSTRACT

The present invention relates to a novel plant enzyme called delta 12 fatty acid acetylenase. This enzyme is responsible for the conversion of fatty acids to acetylenic acids and the invention relates to production of such acids. The invention also relates to use of cDNA encoding acetylenase, preferably Crepis alpina delta 12 acetylenase, for transforming organisms such as oil accumulating organisms selected from the group consisting of oil crops, oleogeneous yeasts and moulds. Furthermore, the invention relates to organisms such as oil accumulating organisms transformed with acetylenase cDNA, and to oils and other acetylenic compounds from said organisms.

8 Claims, 11 Drawing Sheets

Figure 1:
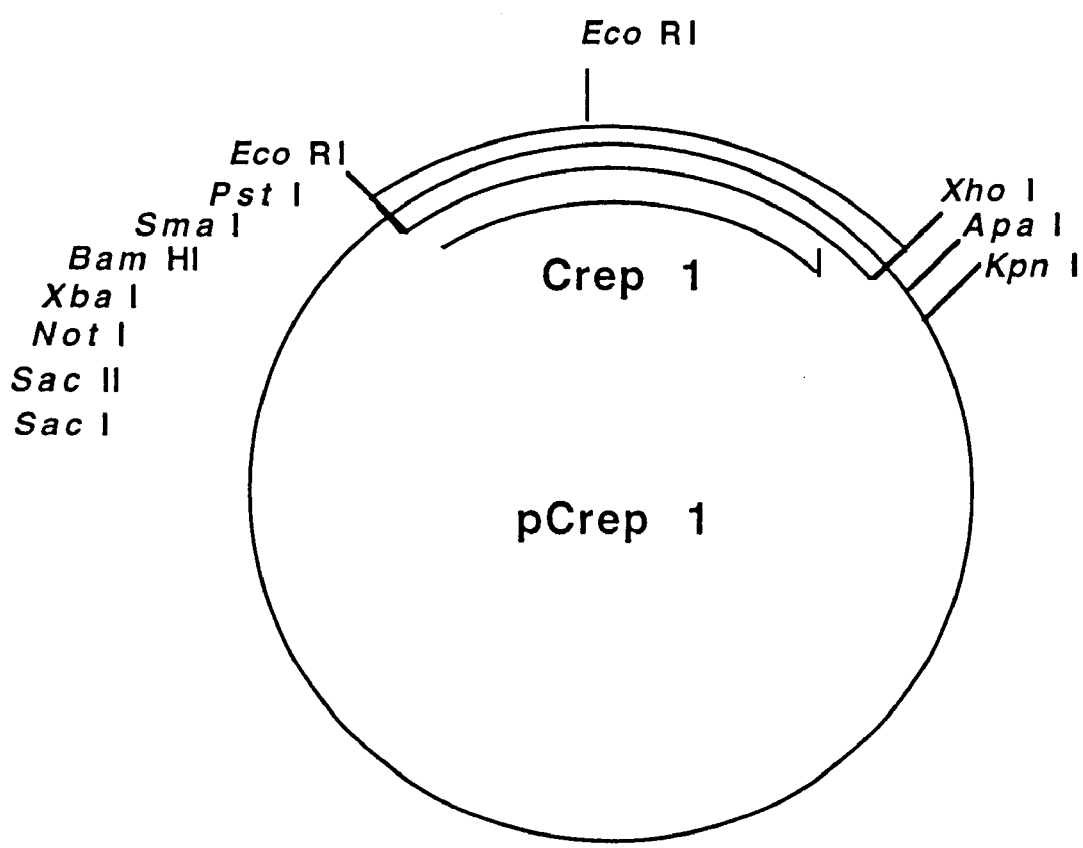

```
                    1                                                                50
bnom6des.seq   .......... ..........  ....MASRIA DSLFAFTGPQ QCLPRAPKLA
gmom6des.seq   .......... ..........  ....MACTLA DSLLLFKGSY Q.KPVLRRDI
atom3des.seq   .MANLVLSEC GIRPLPRIYT TPRSNFLSNN N...KFRPSL SSSSYKTSSS
bnom3des.seq   .......... .......... .......... .......... ..........
rcom3des.seq   MAAGWVLSEC GLRPLPRIYS RPRIGFTSKT TNLLKLRELP DSKSYNLCSS
siom3des.seq   .MASWVLSEC GLRPLPRVYP KPRTGHPLLN SNPTKLRFSR TDLGNGSS..
ldd15des.seq   .MASWVLSQY ALNPLPHIFR TPRTSITSHK .........L TVSHTNNRAT
gsom3des.seq   .MATWYHQKC GLKPLAPVIP RPRTGAALSS TSRVEF.... ..LDTNKVVA
atom3bdes.seq  .......... .......... .......... .......... ..........
bnom31des.seq  .......... .......... .......... .......... ..........
gsom3bdes.seq  .......... .......... .......... .......... ..........
atdl2des.seq   .......... .......... .......... .......... ..........
gmom6bdes.seq  .......... .......... .......... .......... ..........
scom12des.seq  .......... .......... .......... .......... ..........
gmom6ades.seq  .......... .......... .......... .......... ..........
    rchyd.seq  .......... .......... .......... .......... ..........
       crepis  .......... .......... .......... .......... ..........

51                                                               100
bnom6des.seq   SARLSPGVYA VRPIDLLLKG TRRTFLVPAK KRIGCIKAVF VPVAPPSADN
gmom6des.seq   AARYSPGIFS LNSNGLIQKR FRRQRNFVTR NKVTVIHAVA IPVQPAPVES
atom3des.seq   PLSFGLNSRD GFTRNWALNV STPLTTPIFE ESP....... ....LEEDNK
bnom3des.seq   .......... .......... .......... .......... ..........
rcom3des.seq   FKVSSWSNSK QSNWALNVAV PVNVSTVSGE DDREREEFNG IVN.VDEGKG
siom3des.seq   ...FCLSSGI LREKNWALRV SAPLRVLQVE EEEENKEGER VIN.GGEE..
ldd15des.seq   PDLTKLSLIK FRERKLGLRV SAPFQIASTT PE........ .....EEDEV
gsom3des.seq   GPKFQPLRCN LRERNWGLKV SAPLRVASIE EEQKSVDLTN GTNGVEHEKL
atom3bdes.seq  .......... .......... .......MVV AMDQRTNVNG DPGAGDRKKE
bnom31des.seq  .......... .......... .......MVV AMDQRSNANG D.........
gsom3bdes.seq  .......... .......... ........MV KDTKPLAYAA NNGYQQKGSS
atdl2des.seq   .......... .......... .......MGAG GRMPVP.... TSSKKSETDT
gmom6bdes.seq  .......... .......... ......MGAG GRTDVP.... PANRKSEVDP
scom12des.seq  .......... .......... ......MGAG GRMSAP.... NGETEVKRNP
gmom6ades.seq  .......... .......... MGLAKETTMG GRGRVA.... KVEVQGK.KP
    rchyd.seq  .......... .......... ......MGGG GRMSTVITSN NSEKKGGSSH
       crepis  .......... .......... ......MGGG GR........ ..GRTSQKPL 101                                                               150
bnom6des.seq   AEDREQLAES YGFKQIGQDL PDNVTLKDIM DTLPKEVFEI DDVKAWKSVL
gmom6des.seq   AEYRKQLAED YGFRQVGEPL SDDVTLKDVI NPLPKEVFEI DDVKAWKSVL
atom3des.seq   QRFDPGAPPP FNLADIRAAI PKHCWVKNPW KSLSYVVRDV AIVFA.....
bnom3des.seq   .......... .......... .......... ..MSYVVREL AIVFA.....
rcom3des.seq   EFFDAGAPPP FTLADIRAAI PKHCWVKNPW RSMSYVLRDV VVVFG.....
siom3des.seq   ..FDPGAPPP FKLSDIREAI PKHCWVKDPW RSMGYVVRDV AVVFG.....
ldd15des.seq   AEFDPGSPPP FKLADIRAAI PKHCWVKNQW RSMSYVVRDV VIVLG.....
gsom3des.seq   PEFDPGAPPP FNLADIRAAI PKHCWVKDPW RSMSYVVRDV IAVFG.....
atom3bdes.seq  ERFDPSAQPP FKIGDIRAAI PKHCWVKSPL RSMSYVVRDI IAVAA.....
bnom31des.seq  ERFDPSAQPP FKIGDIRAAI PKHCWVKSPL RSMSYVARDI FAVVA.....
gsom3bdes.seq  FDFDPSAPPP FKIAEIRASI PKHCWVKNPW RSLSYVLRDV LVIAA.....
atdl2des.seq   TKRVPCEKPP FSVGDLKKAI PPHCFKRSIP RSFSYLISDI IIASC.....
gmom6bdes.seq  LKRVPFEKPQ FSLSQIKKAI PPHCFQRSVL RSFSYVVYDL TIAFC.....
scom12des.seq  LQKVPTSKPP FTVGDIKKAI PPHCFQRSLI RSFSYVVYDL ILVSI.....
gmom6ades.seq  LSRVPNTKPP FTVGQLKKAI PPHCFQRSLL TSFSYVVYDL SFAF......
    rchyd.seq  LKRAPHTKPP FTLGDLKRAI PPHCFERSFV RSFSYVAYDV CLSFL.....
       crepis  MERVSVD.PP FTVSDLKQAI PPHCFKRSVI RSSYYIVHDA IIAYI.....
```

Figure 8A

SEQUENCE LISTING 1 (cont.)

```
                                                                              200
bnom6des.seq   ISVTSYALGL FMIAKAPWYL LPLAWAWTGT AVTGFFVIGH DCAHKSFSKN
gmom6des.seq   ISVTSYALGL FMISKAPWYL LPLAWVVTGT AITGFFVIGH DCAHRSFSSN
atom3des.seq   LAAGAAYL..  .....NNWIV WPLYWLAQGT MFWALFVLGH DCGHGSFSND
bnom3des.seq   LAAGAAYL..  .....NNWLV WPLYWIAQGT MFWALFVLGH DCGHGSFSND
rcom3des.seq   LAAVAAYF..  .....NNWVA WPLYWFCQGT MFWALFVLGH DCGHGSFSNN
siom3des.seq   LAAVAAYF..  .....NNWVV WPLYWFAQST MFWALFVLGH DCGHGSFSND
ldd15des.seq   LAAAAVAA..  .....NSWAV WPLYWVAQGT MFWALFVLGH DCGHGSFSNN
gsom3des.seq   LAAAAAYL..  .....NNWLV WPLYWAAQGT MFWALFVLGH DCGHGSFSNN
atom3bdes.seq  LAIAAVYV..  .....DSWFL WPLYWAAQGT LFWAIFVLGH DCGHGSFSDI
bnom31des.seq  LAVAAVYF..  .....DSWFF WPLYWAAQGT LFWAIFVLGH DCGHGSFSDI
gsom3bdes.seq  LVAAAIHF..  .....DNWLL WLIYCPIQGT MFWALFVLGH DCGHGSFSDS
atdl2des.seq   FYYVATNYFS LLPQPLSYLA WPLYWACQGC VLTGIWVIAH ECGHHAFSDY
gmom6bdes.seq  LYYVATHYFH LLPGPLSFRG MAIYWAVQGC ILTGVWVIAH ECGHHAFSDY
scom12des.seq  MYYVANTYFH LLPSPYCYIA WPIYWICQGC VCTGIWVNAH ECGHHAFSDY
gmom6ades.seq  IFYIATTYFH LLPQPFSLIA WPIYWVLQGC LLTGVWVIAH ECGHHAFSKY
rchyd.seq      FYSIATNFFP YISSPLSYVA WLVYWLFQGC ILTGLWVIGH ECGHHAFSEY
crepis         FYFLADKYIP ILPAPLAYLA WPLYWFCQAS ILTGLWVIGH ECGHHAFSDY 201                                                            250
bnom6des.seq   KLVEDIVGTL AFLPLVYPYE PWRFKHDRHH AKTNMLVHDT AWQPVPPEEF
gmom6des.seq   KLVEDIVGTL AFMPLIYPYE PWRFKHDRHH AKTNMLREDT AWHPVWKDEF
atom3des.seq   PKLNSVVGHL LHSSILVPYH GWRISHRTHH QNHGHVENDE SWHPMSEKIY
bnom3des.seq   PRLNSVVGHL LHSSILVPYH GWRISHRTHH QNHGHVENDE SWHPMSEKIY
rcom3des.seq   PKLNSVVGHL LHSSILVPYH GWRISHRTHH QNHGHVENDE SWHPLSEKIF
siom3des.seq   PKLNSVVGHI LHSSILVPYH GWRISHRTHH QNHGHVENDE SWHPLSEKIY
ldd15des.seq   HKLNSVVGHL LHSSILVPYH GWRISHRTHH QNHGHVENDE SWHPMSEKLF
gsom3des.seq   SKLNSVVGHL LHSSILVPYH GWRIRHRTHH QNHGHVENDE SWHPMSEKLF
atom3bdes.seq  PLLNSVVGHI LHSSILVPYH GWRISHRTHH QHHGHAENDE SWHPLPEKLF
bnom31des.seq  PLLNTAVGHI LHSFILVPYH GWRISHRTHH QNHGHVENDE SWVPLPERVY
gsom3bdes.seq  PLLNSLVGHI LHSFILVPYH GWRISHRTHH QNHGHVENDE SWVPLPEKLY
atdl2des.seq   QWLDDTVGLI LHSSILVPYH GWRISHRTHH QNHGHIEKDE SWVPLTEKIY
gmom6bdes.seq  QLLDDIVGLI FHSFLLVPYF SWKYSHRRHH SNTGSLERDE VFVPKQKSAI
scom12des.seq  QWVDDTVGLI LHSALLVPYF SWKYSHRRHH SNTGSLERDE VFVPKQKSCI
gmom6ades.seq  QWVDDVVGLT LHSTLLVPYF SWKYSHRRHH SNTGSLERDE VFVPKPKSQL
rchyd.seq      QLADDIVGLI VHSALLVPYF SWKISHRRHH SNTGSLDRDE VFVPKPKSKV
crepis         QWVDDTVGFI LHSFLMTPYF SWKYSHRNHH ANTNSLDNDE VYIPKSKAKV 251                                                            300
bnom6des.seq   DS........ .SPVLRKAII FGYGPIRPWL SI......AH WVNWHFNLRK
gmom6des.seq   ES........ .TPLLRKAII YGYGPFRCWM SI......AH WLMWHFDLKK
atom3des.seq   NTLDK..... PTRFFRFTLP LVMLAYPFYL WARSPGKK.. ..GSHYHPDS
bnom3des.seq   KSLDK..... PTRFFRFTLP LVMLAYPFYL WARSPGKK.. ..GSHYHPDS
rcom3des.seq   KSLDN..... VTKTLRFSLP FPMLAYPFYL WSRSPGKK.. ..GSHYHPDS
siom3des.seq   KNLDT..... ATKKLRFTLP FPLLAYPIYL WSRSPGKQ.. ..GSHFHPDS
ldd15des.seq   RSLTK..... IALTFRFKAP FPMLAYPFYL WERSPGKT.. ..GSHFHPDS
gsom3des.seq   RSLDT..... VTRMLRFTAP FPLLAFPVYL FSRSPGKT.. ..GSHYHPDS
atom3bdes.seq  KKLPH..... STRMLRYTVP LPMLAYPLYL CYRSPGKE.. ..GSHFDPSS
bnom31des.seq  KNLSH..... STRMLRYTVP LPMLAYPLYL WYRSPGKE.. ..GSHYNPYS
gsom3bdes.seq  KNLDS..... MTRLIRFTVP FPLFVYPIYL FSRSPGKE.. ..GSHFNPYS
atdl2des.seq   KWYGKYLNNP LGRIMMLTVQ F.VLGWPLYL AFNVSGRPYD GFACHFFPNA
gmom6bdes.seq  KWYSKYLNNP PGRVLTLAVT L.TLGWPLYL ALNVSGRPYD RFACHYDPYG
scom12des.seq  GWYSKYLNNP PGRVLSLTIT L.TLGWPLYL AFNVSGRPYD RFACHYDPYG
gmom6ades.seq  AWFSKYLNNP LGRAVSLLVT L.TIGWPMYL AFNVSGRPYD SFASHYHPYA
rchyd.seq      SWYSKYSNNP PGRVLTLAAT L.LLGWPLYL AFNVSGRPYD RFACHYDPYG
crepis         ALYYKVLNHP PGRLLIMFIT F.TLGFPLYL FTNISGKKYE RFANHFDPMS
```

Figure 8B

SEQUENCE LISTING 1 (cont.)

```
                    301                                                                      350
bnom6des.seq        ..FRPSEVNR  VKISLACVFA  FMAVGWPLII  YKVGVLGWVK  FWLMPWLGYH
gmom6des.seq        ..FRPSEVPR  VKISLACVFA  FIAIGWPLII  YKTGIMGWIK  FWLMPWLGYH
atom3des.seq        DLFLPKERKD  VLTSTACWTA  .MAALLVCLN  FTIGPIQMLK  LYGIPYWINV
bnom3des.seq        DLFLPKERND  VLTSTACWTA  .MAVLLVCLN  FVMGPMQMLK  LYVIPYWINV
rcom3des.seq        GLFVPKERKD  IITSTACWTA  .MAALLVYLN  FSMGPVQMLK  LYGIPYWIFV
siom3des.seq        DLFVPNEKKD  VITSTVCWTA  .MLALLVGLS  FVIGPVQLLK  LYGIPYLGNV
ldd15des.seq        DLFVPSEKKD  VITSTICWTT  .MVGLLIGLS  FVMGPIQILK  LYVVPYWIFV
gsom3des.seq        DLFVPNERKD  VITSTACWAA  .MLGLLVGLG  FVMGPIQLLK  LYGVPYVIFV
atom3bdes.seq       SLFAPSERKL  IATSTTCWSI  .MFVSLIALS  FVFGPLAVLK  VYGVPYIIFV
bnom31des.seq       SLFAPSERKL  IATSTTCWSI  .MLATLVYLS  FLVGPVTVLK  VYGVPYIIFV
gsom3bdes.seq       NLFPPSERKG  IAISTLCWAT  .MFSLLIYLS  FITSPLLVLK  LYGIPYWIFV
atdl2des.seq        PIYNDRERLQ  IYLSDAGILA  .VCFGLYRYA  AAQGMASMIC  LYGVPLLIVN
gmom6bdes.seq       PIYSDRERLQ  IYISDAGVLA  .VVYGLFRLA  MAKGLAWVVC  VYGVPLLVVN
scoml2des.seq       PIYNNRERLQ  IFISDAGVLG  .VCYLLYRIA  LVKGLAWLVC  VYGVPLLVVN
gmom6ades.seq       PIYSNRERLL  IYVSDVALFS  .VTYSLYRVA  TLKGLVWLLC  VYGVPLLIVN
rchyd.seq           PIFSERERLQ  IYIADLGIFA  .TTFVLYQAT  MAKGLAWVMR  IYGVPLLIVN
crepis              PIFKERERFQ  VLLSDLGLLA  .VLYGVKLAV  AAKGAAWVTC  IYGIPVLGVF 351                                                                      400
bnom6des.seq        FWMSTFTMVH  HTAPH..IPF  KPADEWNAAQ  AQLNGTVHCD  YPSWIEILCH
gmom6des.seq        FWMSTFTMVH  HTAPY..IPF  KYSEEWNRAQ  AQLNGTVHCD  YPKWIEILCH
atom3des.seq        MWLDFVTYLH  HHGHEDKLPW  YRGKEWSYLR  GGL.TTLDRD  YGLINNIHHD
bnom3des.seq        MWLDFVTYLH  HHGHEDKLPW  YRGKEWSYLR  GGL.TTLDRD  YGLINNIHHD
rcom3des.seq        MWLDFVTYLH  HHGHEDKLPW  YRGKAWSYLR  GGL.TTLDRD  YGWINNIHHD
siom3des.seq        MWLDLVTYLH  HHGHEDKLPW  YRGKEWSYLR  GGL.TTLDRD  YGWINNIHHD
ldd15des.seq        MWLDFVTYLD  HHGHEDKLPW  YRGEEWSYLR  GGL.TTLDRD  YGLINNIHHD
gsom3des.seq        MWLDLVTYLH  HHGHEDKLPW  YRGKEWSYLR  GGL.TTLDRD  YGWINNIHHD
atom3bdes.seq       MWLDAVTYLH  HHGHDEKLPW  YRGKEWSYLR  GGL.TTIDRD  YGIFNNIHHD
bnom31des.seq       MWLDAVTYLH  HHGHDDKLPW  YRGKEWSYLR  GGL.TTIDRD  YGIFNNIHHD
gsom3bdes.seq       MWLDFVTYLH  HHGHHQKLPW  YRGKEWSYLR  GGL.TTVDRD  YGWIYNIHHD
atdl2des.seq        AFLVLITYLQ  H..THPSLPH  YDSSEWDWLR  GAL.ATVDRD  YGILNKVFHN
gmom6bdes.seq       GFLVLITFLQ  H..THPALPH  YTSSEWDWLR  GAL.ATVDRD  YGILNKVFHN
scoml2des.seq       GFLVLITYLQ  H..THPSLPH  YDSTEWDWLR  GAL.ATCDRD  YGVLNKVFHN
gmom6ades.seq       GFLVTITYLQ  H..THFALPH  YDSSEWDWLK  GAL.ATMDRD  YGILNKVFHH
rchyd.seq           CFLVMITYLQ  H..THPAIPR  YGSSEWDWLR  GAM.VTVDRD  YGVLNKVFHN
crepis              IFFDIITYLH  H..THLSLPH  YDSSEWNWLR  GAL.STIDRD  FGFLNSVLHD 401                                                                      450
bnom6des.seq        DINVHIPHHI  SPRIPSYNLR  AAHQSIQENW  GKYTNLATWN  WRLMKTIMTV
gmom6des.seq        DINVHIPHHI  SPRIPSYNLR  AAHKSLQENW  GQYLNEASWN  WRLMKTIMTV
atom3des.seq        I.GTHVIHHL  FPQIPHYHLV  EATEAAKPVL  GKYYREPDKS  .GPLPLHLLE
bnom3des.seq        I.GTHVIHHL  FPQIPHYHLV  EATEAAKPVL  GKYYREPDKS  .CPLPLHLLG
rcom3des.seq        I.GTHVIHHL  FPQIPHYHLV  EATEAAKPVM  GKYYREPKKS  .GPLPLHLLG
siom3des.seq        I.GTHVIHHL  FPQIPHYHLI  EATEAAKPVL  GKYYREPKKS  .APLPFHLLG
ldd15des.seq        I.GTHVIHHL  FPQIPHYHLV  EATQAAKPIF  GKYYKEPAKS  .KPLPFHLID
gsom3des.seq        I.GTHVIHHL  FPQIPHYHLV  EATEAAKPVF  GKYYREPKKS  AAPLPFHLIG
atom3bdes.seq       I.GTHVIHHL  FPQIPHYHLV  DATKAAKHVL  GRYYREPKTS  .GAIPIHLVE
bnom31des.seq       I.GTHVIHHL  FPQIPHYHLV  DATKSAKHVL  GRYYREPKTS  .GAIPIHLVE
gsom3bdes.seq       I.GTHVIHHL  FPQIPHYHLV  EATQAAKPVL  GDYYREPERS  .APLPFHLIK
atdl2des.seq        ITDTHVAHHL  FSTMPHYNAM  EATKAIKPIL  GDYYQFDGTP  .......WYV
gmom6bdes.seq       ITDTHVAHHL  FSTMPHYHAM  EATKAIKPIL  GEYYRFDETP  .......FVK
scoml2des.seq       ITDTHVVHHL  FSTMPHYNAM  EATKAVKPLL  GDYYQFDGTP  .......IYK
gmom6ades.seq       ITDTHVAHHL  FSTMPHYHAM  EATNAIKPIL  GEYYQFDDTP  .......FYK
rchyd.seq           IADTHVAHHL  FATVPHYHAM  EATKAIKPIM  GEYYRYDGTP  .......FYK
crepis              VTHTHVMHHL  FSYIPHYHAK  EARDAINTVL  GDFYKIDRTP  .......ILK
```

Figure 8C

```
              451                                             493
bnom6des.seq  CHVYDKEENY IPFDRLAPEE SQPITFLKKA MPDYAA.... ...
gmom6des.seq  CQVYDKEKSL CCLRRTCP.. .......... .......... ...
atom3des.seq  ILAKSIKEDH YV.....SDE GEVVYYKADP NLYGEVKVRA D..
bnom3des.seq  ILAKSIKEDH FV.....SDE GDVVYYEADP NLYGEIKVTA E..
rcom3des.seq  SLVRSMKEDH YV.....SDT GDVVYYQKDP KLSGIGGEKT E..
siom3des.seq  DLTRSLKRDH YV.....SDV GDVVYYQTDP QLTGAEKS.. ...
ldd15des.seq  VLLKSLKRDH FV.....PDT GDIVYYQSDP QISGSLKPE. ...
gsom3des.seq  EIIRSFKTDH FV.....SDT GDVVYYQTDS KINGSSKLE. ...
atom3bdes.seq SLVASIKKDH YV.....SDT GDIVFYETDP DLYVYASDKS KIN
bnom31des.seq SLVASIKKDH YV.....SDT GDIVFYETDP DLYVYASDKS KIN
gsom3bdes.seq YLIQSMRQDH FV.....SDT GDVVYYQTDS LLLHSQRD.. ...
atd12des.seq  AMYREAKECI YVEPDREGDK KGVYWYNNKL .......... ...
gmom6bdes.seq AMWREARECI YVEPDQSTES KGVFWYNNKL .......... ...
scom12des.seq EMWREAKECL YVEKDESSQG KGVFWYKNKL .......... ...
gmom6ades.seq ALWREARECL YVEPDEGTSE KGVYWYRNKY .......... ...
     rchyd.seq ALWREAKECL FVEPDEGAPT QGVFWYRNKY .......... ...
        crepis AMWREAKECI FIEPEKGRES KGVYWY.NKF .......... ...
```

Figure 8D

PLANT ENZYME AND USE THEREOF

This is a CIP of parent, co-pending application PCT/SE97/00247, filed Feb. 14, 1997, the entire contents of which are hereby incorporated by reference.

TECHNICAL FIELD

The present invention relates to a novel plant enzyme. More specifically, the present invention relates to a method for producing acetylenic compounds in particular acetylenic fatty acids, to a cDNA encoding a plant fatty acid acetylenase, to the use of the said cDNA for transforming oil accumulating organisms for the purpose of producing acetylenic fatty acids, and to such oil accumulating organisms per se as well as oils therefrom.

BACKGROUND OF THE INVENTION

There is considerable interest, world-wide, in producing chemical feedstocks such as fatty acids for industrial use from renewable plant resources rather than from non-renewable petrochemicals. This concept has broad appeal for both manufacturers and consumers on the basis of resource conservation and in addition provides significant opportunities to develop new industrial crops for agriculture.

There is an enormous diversity of unusual fatty acids in oils from wild plant species which have been well characterized (see e.g. Badami & Patil, 1981). Many of these acids are of potential industrial use. This has lead to an interest in domesticating relevant plant species to enable the agricultural production of particular fatty acids. However the development of genetic engineering combined with a greater understanding of the biosynthesis of unusual fatty acids make it now possible to transfer genes coding for key enzymes, involved in the synthesis of a particular fatty acid from a wild species, to a choosen domesticated oilseed crop. In this way specific fatty acids can be produced in high purity and quantities at moderate costs.

One class of fatty acids of particular interest are the acetylenic fatty acids; consisting of an acyl chain having two adjacent carbon atoms linked by an acetylenic or triple bond. Because of their high reactivities they may be ideally suited for the production of coatings, plastics and lubricants. By transferring the genes responsible for the production of a specific acetylenic acid from a wild species to commercial oilseeds, or any other oil accumulating organism that can be easily multiplied, it should be possible to develop a renewable primary source of this oil containing acetylenic fatty acids for industrial uses.

PRIOR ART

The formation of acetylenic bonds in fatty acids in mosses occurs via the subtraction of hydrogens from a double bond (Kohn et al., 1994)

Crepis species have seed oils with high contents of acetylenic acids (Badami & Patil, 1981; Hirsinger, 1991).

SUMMARY OF THE INVENTION

The present invention provides a new method of producing acetylenic fatty acids from transgenic oil accumulating organisms.

The inventors have characterized an enzyme (acetylenase) that is responsible for the production of 9-octadecen-12-ynoic acid (crepenynic acid) from 9,12-octadecadienoic acid (linoleic acid) in membrane fractions from developing Crepis alpina seeds. The characterization of the acetylenase from Crepis alpina revealed that the acetylenase had very similar biochemical properties to the non-heme containing monooxygenases oleate delta 12 and linoleate delta 15 (omega 3) desaturases. Based on the premise that the biochemical similarities observed between the acetylenase and the enzymes producing linoleic and linolenic acid (delta 12 and delta 15 desaturases) would also be associated with similarity in the primary sequence of these proteins a full length cDNA (pCrep1) (SEQ ID NO:1), encoding a putative acetylenase (SEQ ID NO:2), was isolated from Crepis alpina.

Initially, two types of cDNA fragments, obtained by using PCR and primers designed by aligning protein sequences of delta 12 desaturases, were characterised from C. alpina. DNA sequence analysis revealed that one was highly homologous to all the other plant endoplasmic reticular (ER) delta 12 desaturases and the castor bean hydroxylase. The other cDNA fragment characterised had a sequence that was homologous to the ER delta 12 desaturase sequences of plants but was divergent not only in a number of non-conserved amino residues but also in a number of amino acid residues that were highly conserved in all delta 12 ER desaturases. Using northern blot analysis the gene encoding this cDNA (pCrep1) was observed to be highly expressed only in a seed specific manner when compared to expression in leaf tissue. Taken together these findings, and a consideration of the unique biochemical nature of an cell in a oilseed, provided strong evidence that the isolated cDNA (pCrep1) from C. alpina encode an enzyme responsible for converting linoleic acid into crepenynic acid.

Finally, conclusive evidence that the cDNA, pCrep1, from C. alpina encoded a plant acetylenase enzyme was obtained by the expression of this gene in yeast. The expression of this gene together with the addition of linoleic acid when culturing these yeast resulted in the production of a delta 12 acetylenic acid, 9-octadecen-12-ynoic acid (crepenynic acid), as confirmed by mass spectrometric analysis of extracted yeast fatty acids.

Therefore, in a first aspect, the present invention relates to a method of producing acetylenic compounds, characterized in that a double bond is converted to an acetylenic bond by an acetylenase.

In a preferred embodiment of the method, the acetylenic fatty acids are produced by conversion of unsaturated fatty acids to acetylenic fatty acids by a fatty acid acetylenase.

In a second aspect, the invention relates to cDNA coding for acetylenase of the mixed function monoxygenase type containing three conserved histidine motifs (His $Xaa_{(3\ or\ 4)}$His and His $Xaa_{(2\ or\ 3)}$His His, and His $Xaa_{(2\ or\ 3)}$His His) according to FIGS. 8A–8D of the accompanying drawings.

Figure 3:
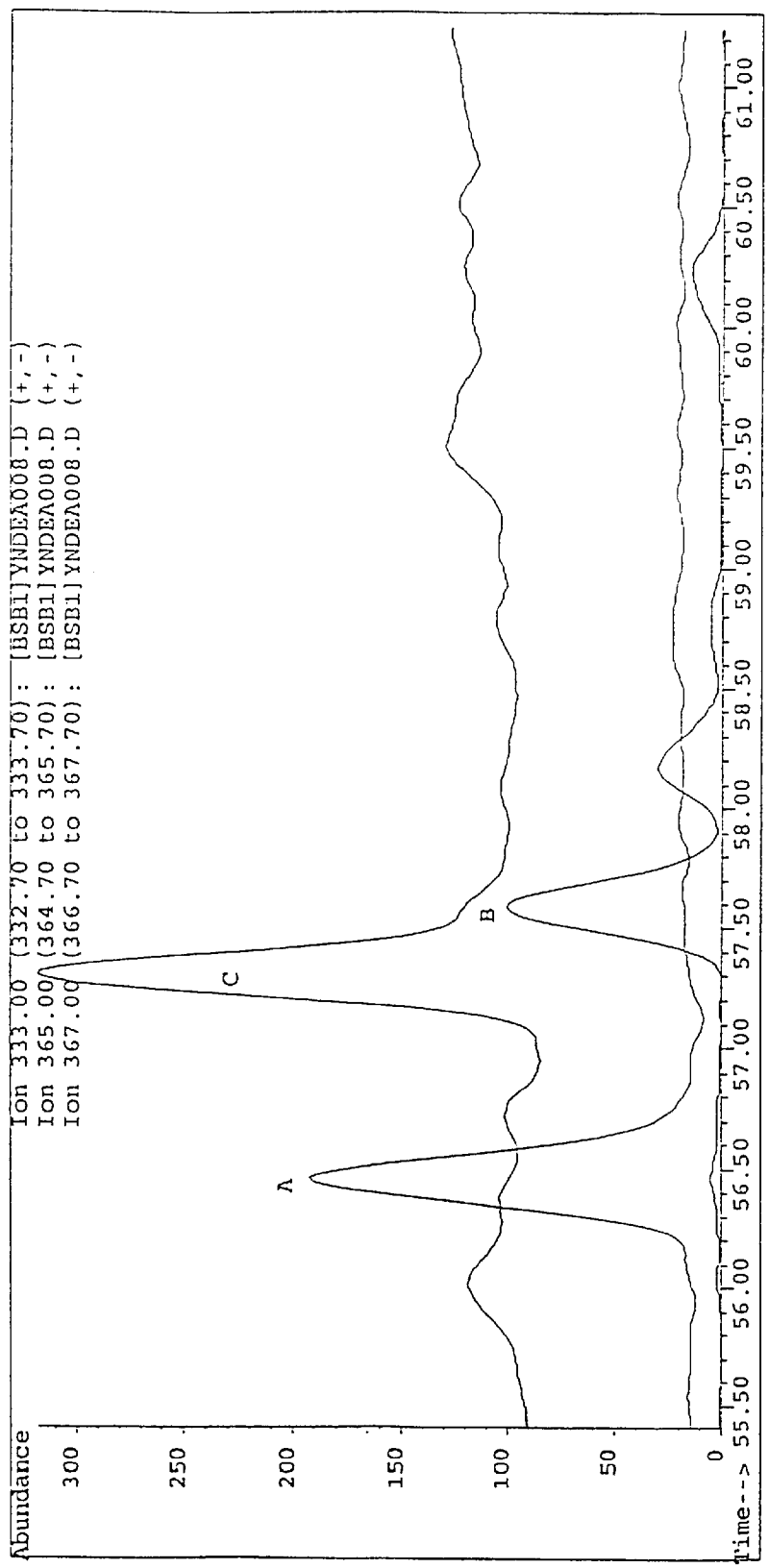

In a further embodiment the invention relates to a cDNA encoding fatty acid acetylenase, such as Crepis alpina delta 12 acetylenase comprising the sequence according to FIG. 3 of the accompanying drawings or any nucleotide sequences essentially homologous therewith.

A third aspect of the invention concerns use of the above described cDNA for transforming organisms. The organisms may be acetylenic compound accumulating organisms or oil accumulating organisms, respectively.

In a fourth aspect, the invention relates to organisms transformed with a acetylenase CDNA as described above. The organisms are acetylenic compound or oil accumulating, examples of the latter being oil crops, oleaginous yeasts and moulds.

In a fifth aspect, the invention concerns acetylenic componds accumulated in organisms described above.

In a sixth aspect, the invention concerns oils from oil accumulating organisms described above.

In a preferred embodiment, the present invention relates to transforming oil accumulating organisms with the said isolated cDNA from *Crepis alpina* seed cDNA library for the purpose of producing acetylenic fatty acids acids and in particular 9-octadecen-12-ynoic acid (crepenynic acid).

DETAILED DESCRIPTION OF THE INVENTION

*C. alpina* seed oil is rich in crepenynic acid [0-octadecen12-ynoic acid (Hirsinger, 1989)]. The inventors have studied the biosynthesis of crepenynic acid in *C. alpina* seeds. The feeding of exogenous 1-$^{14}$C-labelled free fatty acids to intact developing cotyledons of *C. alpina* seeds demonstrated that linoleate is a precursor to crepenynic acid. This is contradictory to previous published results for the biosynthesis of crepenynic acid in *Crepis rubra* (Haigh & James, 1967). Although the reaction of acetylenic acid formation in mosses has been shown to be a desaturation process (Kohn et al. 1994), such desaturation processes can be carried out by a variety of different unrelated types of plant enzymes, such as phytoene desaturases (Wieland et al. 1994) or non-heme containing proteins, the latter a class of enzymes of which some show very little amino acid sequence homologies except for three conserved histidine motifs (Shanklin et al. 1994). It has been suggested that the biosynthesis of acetylenic fatty acids occur by a sequence of intermediates catalyzed by separate enzymatic reactions. For example, acetylenic bonds were thought to be formed as a side pathway of saturated fatty acid synthesis (Diedrich & Henschel, 1991); or via an epoxygenation of a double bond with subsequent conversion to a diol which in its turn is dehydrated in two steps in order to form an acetylenic bond (Van de Loo et al. 1993). Given these conflicting alternatives the nature of an acetylenase enzyme and its mechanism of action was not known at all nor obvious at the time of the present priority patent application SE 9601236-4.

The enzyme, according to this invention, responsible for the synthesis of crepenynic acid (called the delta 12 acetylenase), was shown by the inventors to remain only active in membrane (microsomal) fractions prepared from developing seeds of *Crepis alpina*, provided that the homogenization buffer contain NADH or NADPH, catalase and free coenzyme A. The characterisation of the microsomal acetylenase and its comparison with the delta 12 desaturase (responsible for the desaturation of oleate to linoleate) revealed that these enzymes had very similar properties. Both enzymes required $O_2$ and NADH or NADPH; where both coreductants worked equally well with both enzymes. Cyanide (CN—) and antibodies against cauliflower cytochrome $b_5$ inhibited both these enzymes whereas carbonmonoxide had no significant effect on either enzyme activity. These data suggested that both enzymes were biochemically similar. The oleate delta 12 hydroxylase from castor bean was also shown to have similar biochemical properties to the delta 12 desaturase despite catalyzing a different reaction (Bafor et al., 1991, Smith et al, 1992). The castor bean delta 12 hydroxylase gene was later shown to have significant sequence homology to the ER delta 12 desaturase genes (FAD 2 genes) (Van de Loo et al., 1995). Because the delta 12 acetylenase, like the delta-12 desaturase (FAD2), catalyzes a dehydrogenation between carbons 12 and 13 of an acyl chain, and like the delta 15 desaturase (FAD3) utilized linoleic acid as substrate the inventors considered the possibility that the acetylenase gene should have some sequence homology to the FAD2 and/or the FAD3 genes.

The invention will now be described more closely below in relation to the accompanying drawings and an Experimental Part.

THE DRAWINGS SHOW

FIG. 1. Restriction map of pCrep1

Figure 2:
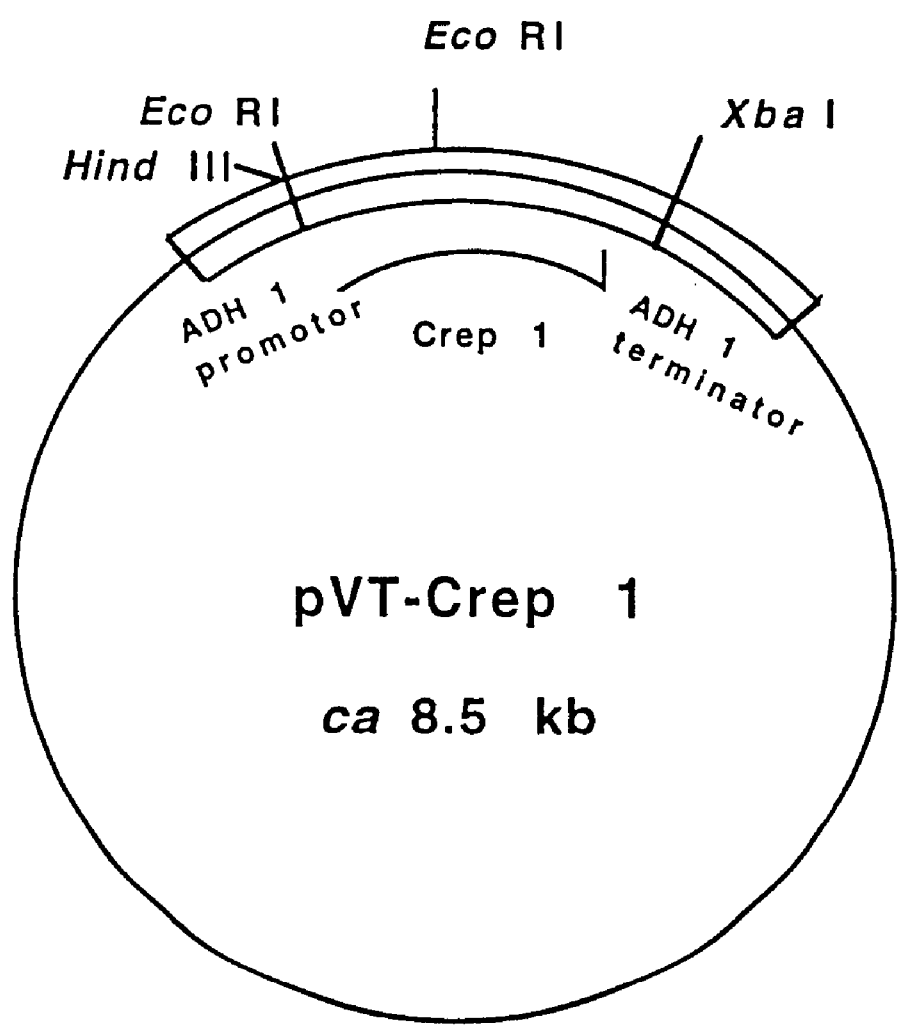

FIG. 2. Restriction map of pVT-Crep1

FIG. 3. Superimposed single ion chromatograms of ions 333, 365, 367 from FADEA prepared from total fatty acids extracted from yeast strain YN94-1 transformed with pVT-Crep1. The letters denotes peaks representing the following diethylamide derivatives of fatty acids: A, eicosanoic acid; B, eicosaenoic acid; C, 9-octadecen-12-ynoic acid.

Figure 4:
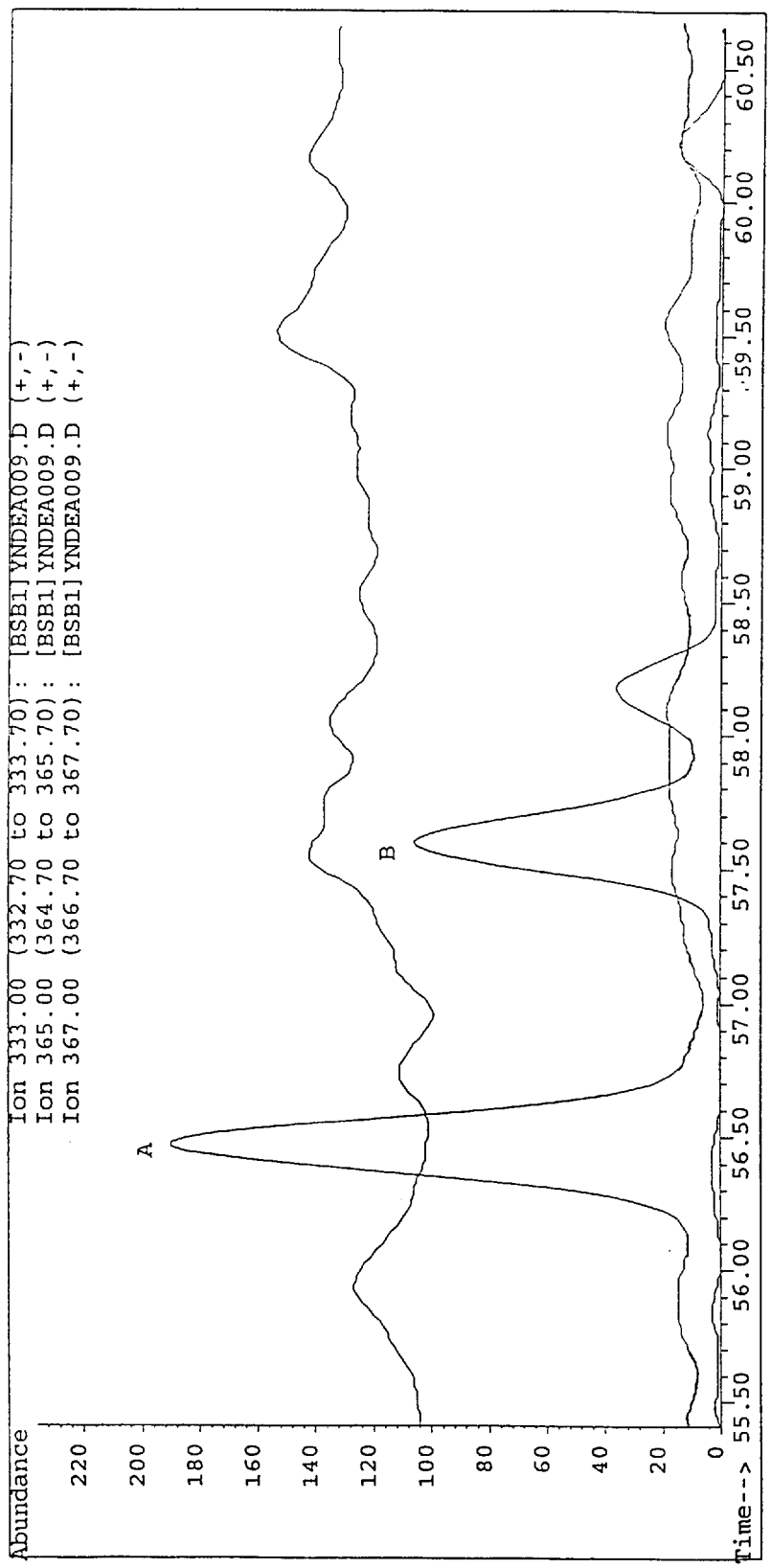

FIG. 4. Superimposed single ion chromatograms of ions 333, 365, 367 from FADEA prepared from total fatty acids extracted from yeast strain YN94-1 transformed with empty vector (pVT100U; control). The letters denotes peaks representing the following diethylamide derivatives of fatty acids: A, eicosanoic acid; B, eicosaenoic acid.

Figure 5:
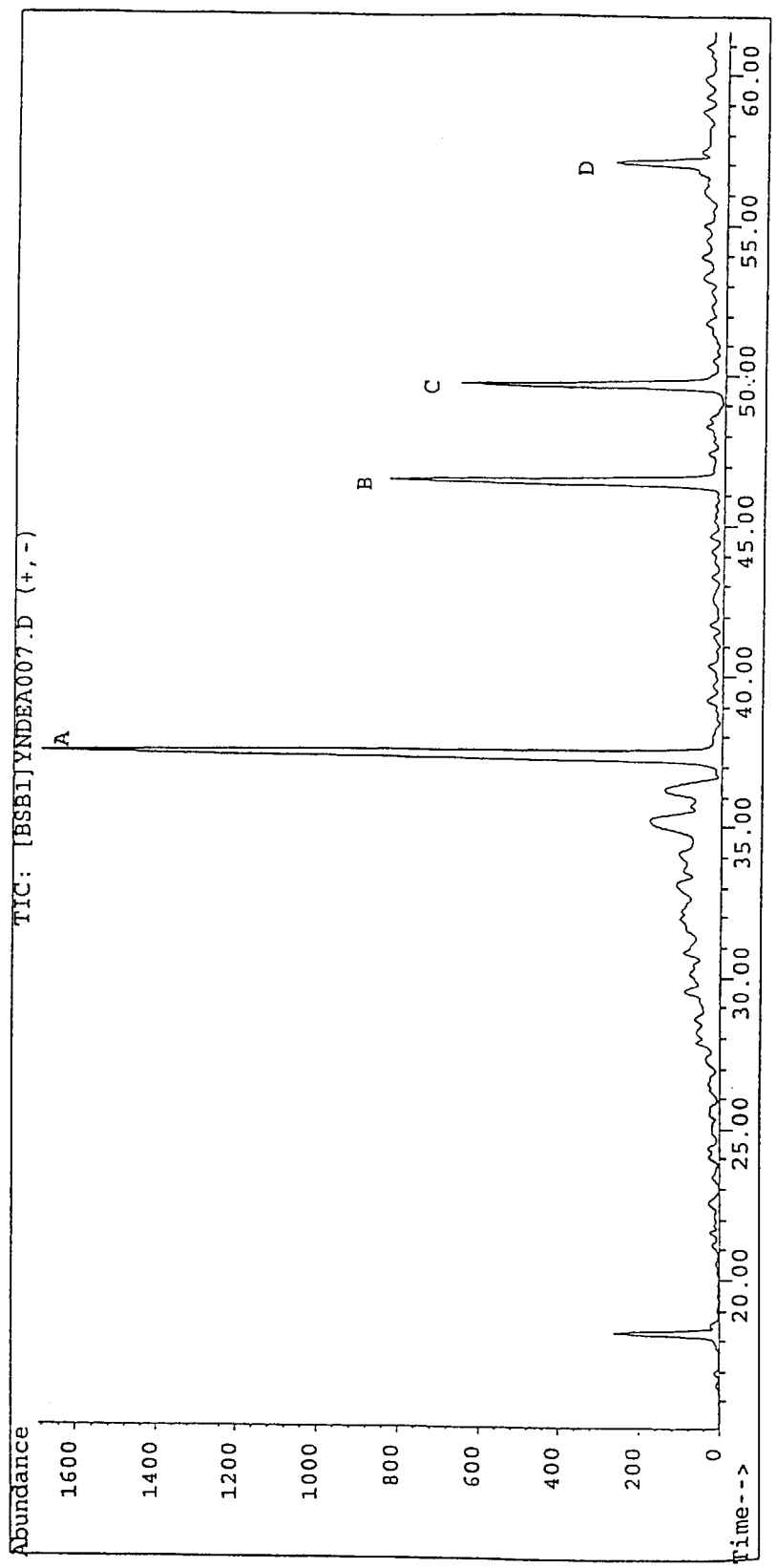

FIG. 5. A total ion chromatogramme of FADEA prepared from fatty acids enriched in the putative 9-octadecen-12 ynoic acid originating from lipid extracts of YN94-1 transformed with pVT-Crep1. The letters denotes peaks representing the following diethylamide derivatives of fatty acids: A, hecadecanoic acid; B, octadecaonoic acid; C, octadeca-9,12-dienoic acid; D. 9-octadecen-12-ynoic acid.

Figure 6:
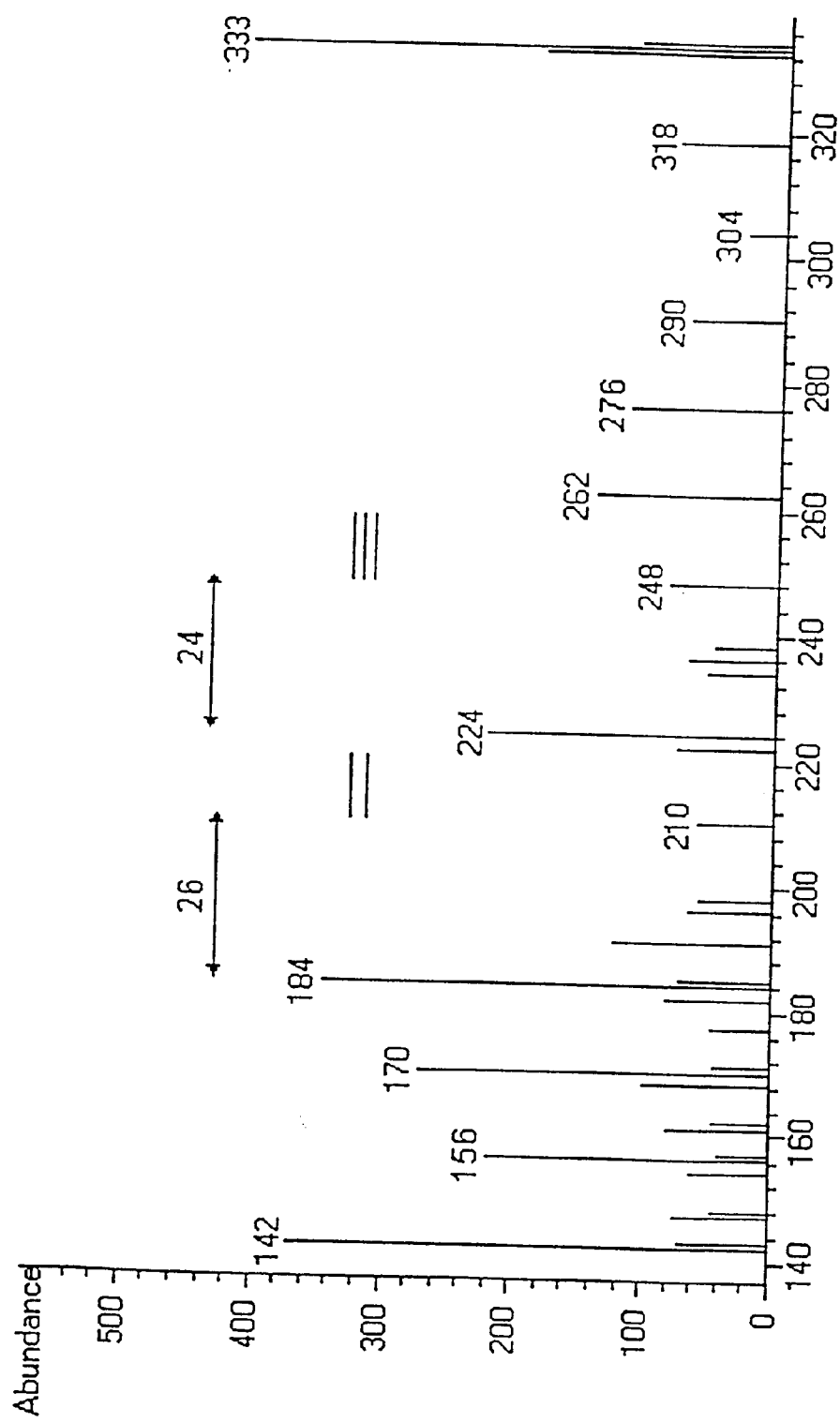

FIG. 6. Mass spectrum of compound corresponding to peak D in FIG. 5.

Figure 7:
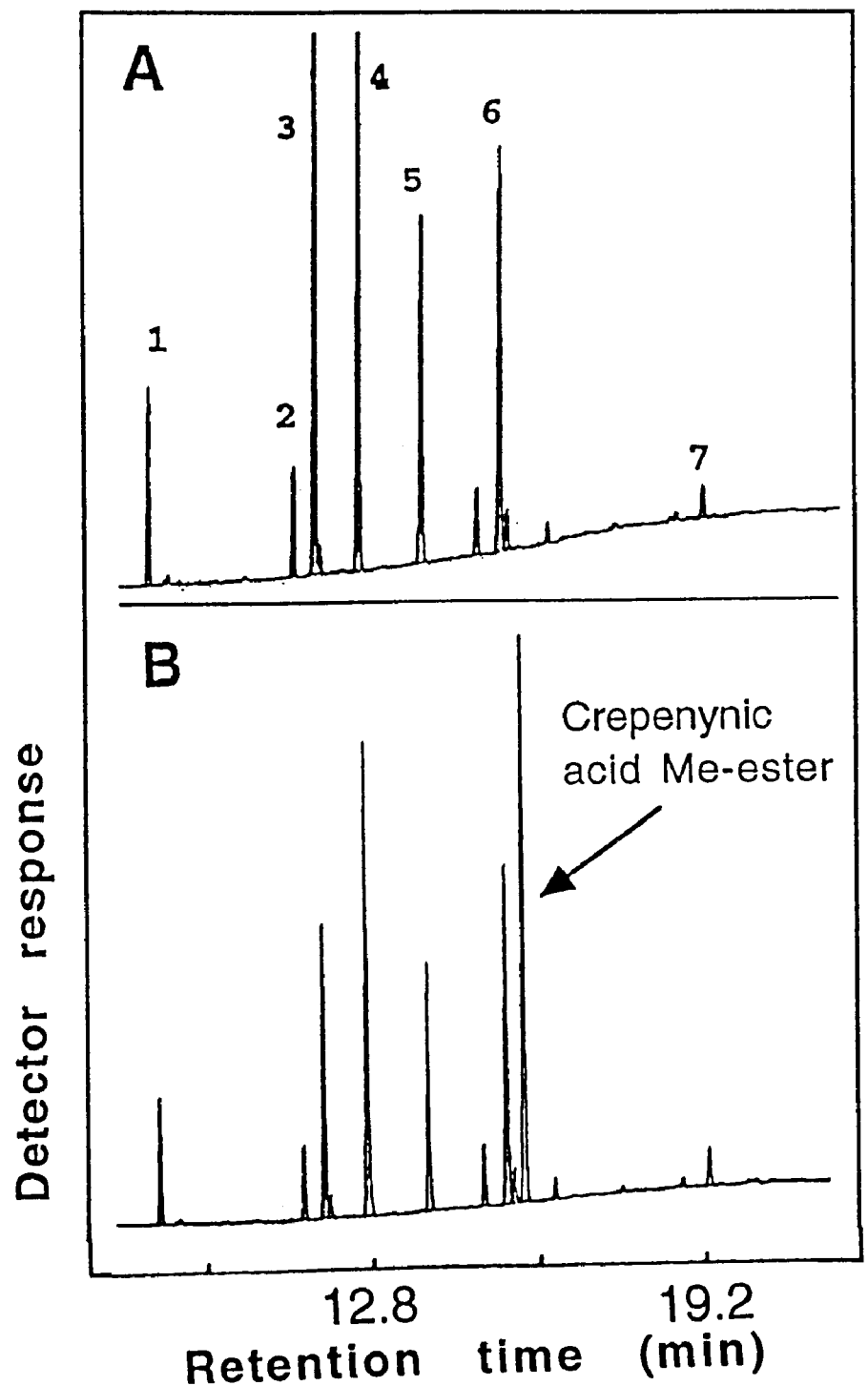

FIG. 7. Gas liquid analysis of *A. thaliana* seed fatty acids. Methyl esters of seeds from a plant transformed with (A) an empty vector and (B) the *Crepis alpina* acetylenase (Crep1) were analyzed and their fatty acid profile determined. In (A) the indicated peaks correspond to methyl esters (Me) derivates of hexadecanoic acid, 1; octadecanoic acid, 2; 9-octadecenoic acid, 3; 9,12-octadecadienoic acid, 4; 9,12, 15-octdecatrienoic acid, 5; 11-eicosaenoic acid, 6 and 13-docosaenoic acid, 7. In (B) the peak corresponding to the methyl ester derivative of crepenynic acid is indicated and corresponds to 25% of total fatty acid methyl ester peak areas.

FIGS. 8A–8D show an alignment of amino acid sequences from delta 12 ER and plastid desaturases, delta 15 desaturases and from the castor bean hydroxylase. Also included in this alignment is the protein sequence derived from pCrep1 (crepis). Underlined are three histidine motifs that are conserved in non-heme containing monoxygenases. Sequences given in this alignment together with their accession numbers are:

bnom6des.seq, delta 12 desaturase from *Brassica napus* (L29214) (SEQ ID NO:3);

gmom6des.seq, delta 12 desaturase from *Glycine max* (L29215) (SEQ ID NO:4);

atom3des.seq, delta 15 desaturase from *Arabidopsis thaliana* (L22961) (SEQ ID NO:5);

bnom3des.seq, delta 15 from *Brassica napus* (L22963) (SEQ ID NO:6);

rcom3des.seq, delta 15 desaturase from *Ricinus communis* (L25897) (SEQ ID NO:7);

siom3des.seq, delta 15 desaturase from oriental sesame (U25817) (SEQ ID NO:8);

ldd15des.seq, delta 15 desaturase from *Limnanthes douglasil* (U17063) (SEQ ID NO:9);

gsom3des, delta 15 desaturase from *Glycine max* (L22965) (SEQ ID NO:10);

atom3bdes.seq, delta 15 desaturase from *Arabidopsis thaliana* (D17579) (SEQ ID NO:11);

bnom31des.seq, delta 15 from *Brassica napus* (L22962) (SEQ ID NO:12);
gsom3bdes.seq, delta 15 desaturase from *Glycine max* (L22964) (SEQ ID NO:13);
atd12des.seq, delta 12 desaturase from *Arabidopsis thaliana* (L26296) (SEQ ID NO:14);
gmom6bdes.seq delta 12 desaturase from *Glycine max* (L43921) (SEQ ID NO:15);
scom12des.seq, delta 12 desaturase from *S. commersonli* (X92847) (SEQ ID NO:16);
gmom6ades.seq, delta 12 desaturase from *Glycine max* (L43920) (SEQ ID NO:17);
rchyd.seq, oleate 12-hydroxylase from *Ricinus communis* (U22378) (SEQ ID NO:18);
crepis, *Crepis alpina* acetylenase from this document (SEQ ID NO:2).

EXPERIMENTAL PART

Cloning of Putative Acetylenase Gene

An alignment of amino acid sequences (SEQ ID Nos:3–18) from different species showed that the membrane bound fatty acid desaturases could be grouped according to the homology of their putative mature protein into three distinct groups (plastid delta 12 desaturases, ER delta 12 desaturases and delta 15 desaturases; see FIGS. 8A–8D). The castor bean hydroxylase (Van de Loo et al 1995) shared a high homology with the ER delta 12 desaturases to the degree that it was not easily distinguishable from these sequences. Furthermore, the sequences from all three classes of enzymes showed some degree of sequence homology with each other.

Based on this alignment oligonucleotide primers were designed and synthesised for these three groups of sequences and for a consensus of all of these sequences. The sequence of these primers are given below.

(i) consensus primers (primers designed to a consensus of all three groups of membrane-bound desaturases and the castor bean fatty acid hydroxylase): sense is GSN CAY GAN TGY GSN CAY (SEQ ID NO:19) antisense is RAN ADR TGR TGN RBN AYR TG (SEQ ID NO:20).
(ii) plastid delta 12 desaturase primers: sense is TGG MGN TTY AAR CAY GAY MG (SEQ ID NO:21) antisense is GTN SWC ATC CAR AAR TGR TA (SEQ ID NO:22).
(iii) ER delta 12 desaturase primers including the castor bean fatty acid hydroxylase: sense is CAY GAR TGY GGN CAY CAY GC (SEQ ID NO:23) antisense is CCN CKN ARC CAR TCC CAY TC (SEQ ID NO:24).
(iv) delta 15 desaturase primers: sense is ACN CAY CAY CARAAY CAY GG (SEQ ID NO:25) antisense is CAY TGY TTN CCN CKR TAC CA (SEQ ID NO:26).

Poly A+ RNA was isolated from developing seeds (100 mg) of *C. alpina* using a QuickPrep Micro mRNA purifcation kit from Pharmacia Biotech. All of the poly A+ RNA from this purification was precipitated and used to synthesise first strand cDNA which was primed with both oligo dT and random hexamers and synthesised with Superscript II reverse transcriptase from Gibco BRL. The polymerase chain reaction (PCR) was then used, with the described primers and this cDNA, to amplify products with the following cycling conditions: 1 cycle of 94° C. for 2 min, 30 cycles of (94° C., 30 sec; 50° C., 30 sec; 72° C., 30 sec) and finally one cycle of 72° C. for 5 min.

Products were obtained for all the primers used; particularly noticeable was that the primers against the ER delta 12 desaturases gave significantly more product than from the other primers used. The sizes of the PCR products from the delta 12 and delta 15 primers corresponded to the sizes anticipated.

The PCR products obtained by amplification with the ER delta 12 primers and delta 15 primers were made blunt ended with T4 and klenow polymerases and cloned into the EcoRV site of the plasmid vector Bluescript. DNA sequencing of a number of the clones revealed that at least three distinct sequences had been amplified when using these two sets of primers: (i) a highly conserved delta 15 desaturase sequence (ii), a highly conserved ER delta 12 sequence and (iii) a sequence (D12V) having homology to the ER delta 12 sequences but showing distinct differences even in some amino acid residues that were highly conserved amongst all the other desaturase sequences.

The analysis of fatty acids from *C. alpina* had indicated that the crepenynic acid was probably present only in seeds. Northern blot analysis at high stringency indicated that the mRNA from the D12V sequence described above was expressed highly in seeds but not in leaves which is consistent with the observation that crepenynic acid was only observed in seeds.

A cDNA library was made from developing seeds from *C. alpina* using a Uni-ZAP XR cloning kit for cDNA from Stratagene and screened with the random labelled D12V sequence. From this screening it was estimated that cDNAs encoding the D12V sequences were highly abundant; further emphasing the high level of expression of this gene. After the isolation of single hybridising Lambda plaques, pBluescript phagemid was excised using the ExAssist/SOLR system from Stratagene, Phagemids obtained by this were subsequently used to produce double stranded DNA plasmid. From these colonies a full length clone (pCREP1, see FIG. 1) was isolated by using DNA sequencing and restriction mapping of isolated plasmid. The insert from pCrep1, a 1.5 kb insert contained in the vector pBluescript SK, was sequenced and from this an open reading frame deduced coding for a 375 aa long protein (SEQ ID NO:2). The analysis of this protein sequence revealed approximately 60% identity and 80% similarity with other plant delta 12 desaturase proteins and had noticeable differences I homology, where, certain residues that were conserved amongst all other desaturases were not in this sequence FIGS. 8A–8D. Three histidine motifs were present which have been shown to be conserved in a number of non-heme containing monoxygenases catalyzing hydroxylation and desaturation reactions (Shanklin et al. 1994).

Expression of the pCrep cDNA and Detection of Crepenynic Acid in Transgenic Yeast The pCrep1 open reading frame was released from pCrep1 on a SmaI/XhoI restriction fragment and the 1.5 kb Crep1 open reading frame recovered by gelpurification (Langridge et al., 1980). pVT100-U DNA (Vernet et al., 1987) was digested using PvuII and XhoI. 50 ng PvuII/XhoI-linearized pVT100 was ligated with 100 ng 1.5 kb SmaI/XhoI fragment corresponding to the Crep1 open reading frame using T4 DNA ligase (NBL Genen Science Ltd., UK). Part of the ligation mixture was used to transform competent *E. coli* DHa cells. One clone (pVT-Crep1), which contained the expected 1.5 kb insert, was chosen and the contruct checked by digestion with EcoRI, or HindIII+XbaI. Both digests gave the expected products (approx. 5.3, 2.3 and 0.8 kb for the EcoRI digest, and release of the 1.5 kb open reading frame with the HindIII+XbaI digest). pVT-Crep1 DNA (see FIG. 2), or empty vector pVT100U, was used to transform *Saccharomyces cerevisiae* strains YN94-1 and C13-ABYS86, using the PLATE method of Elble (1992). Overnight yeast transformants were spread on SCD minus uracil agar and single colonies were streaked onto fresh selective (minus uracil) plates.

The YN94-1 and C13-ABYS86 strains of yeast transformed with pVT-Crep1 DNA and with empty vector (pVT100U; control) were cultivated in shaking cultures at 28° C. for five hours in selective media (without uracil; 400 ml) whereafter 40 ml of cultivation media containing linoleic acid dispersed in Tween 40® was added to the culture to give a final concentration of 0.03% linoleic acid and 1% Tween 40® (w/w). After cultivation for an additional 78 h at 28° C. the cells were pelleted by centrifugation and washed by dispersion in 20 ml of 0.1M Tris-HCl buffer pH. 7.8 containing 1% Tween 40® and repelleted by centrifugation. The cells were further washed by resuspension in 20 ml of 0.1M Tris-HCl buffer pH. 7.8 and pelleted again. The cells were thereafter extracted in a mixture of chloroform/methanol/0.15M acetic acid (1:2:0.8 by vol.) in a Braun MSK glass bead cell homogenizer (B. Braun Biotech International, Melsungen, Germany) at 4000 r.p.m. for 20 s. The yeast lipids were extracted from the mixture into a chloroform phase by adding chloroform and 0.15M acetic acid to yield final proportions of 1:1:0.9 (by vol.) of chloroform, methanol and 0.15 M acetic acid. After centrifugation of the mixture the lipid containing chloroform phase was removed and evaporated to dryness under a stream of nitrogen.

The lipohilic residue were methylated with methanolic HCl (4% w/w) at 85° C. for 45 min wherafter the fatty acid methyl esters were extracted into n-hexane. Gas liquid (GC) chromatogrammes of the methyl esters separated on a glass column (2.5 m×3 mm i.d.) containing 3% SP-2300 on Supelcoport 100/120 mesh (Supelco, Bellefonte, P. USA) revealed a peak with the same retention time as authentic 9-octadecen-12 ynoic acid metyl ester constituting up to 0.3% of total peak areas in samples prepared from yeast transformed with pVT-Crep1 but not in samples prepared from yeast transformed with empty vector (pVT100U; control).

Since acetylenic fatty acid methyl esters can be partially separated from other fatty acid methylesters on silica gel thin layer chromatography, the methylesters prepared from YN94-1 transformed with pVT-Crep1 were separated on silica gel 60 thin layer chromatography plates (Merck, Darmstadt, Germany) by developing the plate in hexane/diethyl ether/acetic acid (85:15:1 by vol.). An area located just below the main methyl ester area was removed from the plate and the lipids were eluted with methanol/chloroform (2:1) and analyzed by gas liquid chromatography. The fraction were shown to consist of fatty acid methylesters where the peak with the same retention time as 9-octadecen-12 ynoic acid metyl ester made up 12.5% of the total peak area.

The methyl ester fraction enriched in the putative 9-octadecen-12 ynoic acid methyl ester as well as total fatty acid methyl esters prepared from YN94-1 transformed with pVT-Crep1 and YN94-1 transformed with empty vector (pVT100U; control) were hydrolyzed in 2.5M KOH in aqueous methanol (15% methanol, by vol.) at 90° C. for 1 h. The free fatty acids were extracted into hexane after acidicifiction with HCl and the hexane phase was evaporated to dryness under a stream of nitrogen.

Fatty acid diethylamides (FADEA) were prepared from the free fatty acids according to Nilsson and Liljenberg (1991). The FADEA were either injected directly on a gas liquid chromatography coupled to mass spectrometer (GC-MS) or subjected to further purification by silica gel thin layer chromatography by developing the plate in heptane/diethyleter/acteic acid (50:50:1, by vol.).

The FADEA were analyzed on a Hewlett-Packard 5890 II gas chromatograph equipped with a DB225 (0.25 mm i.d.× 30 m, J&W, Folsom, USA) in series with a Rtx 2330 (Restek Corp., PA, USA) fused silica capillary column, coupled with a Hewlett-Packard 5989A mass spectrometer working in electron impact mode at 70 eV. Injection technique was cold splitless at 100° C. and then the temperature was raised as quickly as possible to 240° C. Oven temperature was 100° C. for 7 min, then 20° C. per min to 190° C. and then 1° C. per min to a final temp. of 225° C. where it was kept for another 20 min. The double bond positions were determined according to Nilsson and Liljenberg (1991).

Single ion chromatogrammes of masses corresponding to the molecular ion of FADEA prepared from total fatty acids from YN94-1 transformed with pVT-Crep1 and from YN94-1 transformed with empty vector (pVT100U; control) are shown in FIG. 5 and FIG. 6, respectively. Chromatogram of FADEA from YN94-1 transformed with pVT-Crep1 showed a peak of mass 333 (corresponding to the molecular weight of 9-octadecen-12 ynoic acid diethylamide) which was absent in the chromatogram of FADEA from YN94-1 transformed with empty vector (pVT100U; control). The peak had a retention time of 57.3 min and was located between peaks corresponding to eicosanoic and eicosenoic FADEA derivatives.

A total ion chromatogramme of FADEA prepared from fatty acids enriched in the putative 9-octadecen-12 ynoic acid by thin layer chromatography (as described above) originating from lipid extracts of YN94-1 transformed with pVT-Crep1 is shown in FIG. 5. Mass spectrum (FIG. 6) of the putative 9-octadecen-12 ynoic acid diethylamide derivative (peak D in FIG. 5) showed a gap in mass of 26 amu instead of regular 28 between carbon 7 and 9 indicating a double bond at position 9. Further more there was a gap of 24 amu instead of regular 28 between carbon atom 10 and 12 indicating acetylenic bond at position 12. The peak D produced a mass spectrum identical to that of authentic 9-octadecen-12 ynoic acid diethylamide prepared from oils from *Crepis alpina* seeds. Thus the peak D in the chromatogram in FIG. 5 was unambigously identified as 9-octadecen-12 ynoic acid diethylamide derivative. Since the compound was absent in yeast strains not transformed with the Crep1 cDNA it is clear that the Crep1 cDNA codes for a delta-12 fatty acid acetylenase.

Production of Acetylenic Fatty Acids in Seed Oils of Transgenic Plants

The Crep1 gene was expressed in Arabidopsis under control of the seed-specific napin promoter. Total fatty acids of bulk seed samples from individual $T_0$ transgenic plants consisted up to 25% crepenynic acid, with no other acetylenic fatty acids being detected while plants transformed with empty vector had no acetylenic acids in their seeds (FIG. 7).

Experimental

A binary vector for the acetylenase consisted of the Crep1 cDNA placed downstream of the −309 fragment from the napin promoter (Stalberg et al., 1993) in the vector pGPTV-KAN (Becker et al., 1992). *A. thaliana* columbia (C-24) was transformed with *Agrobacterium tumefaciens* (Valvekens, 1988). Methyl esters of seed fatty acids from $T_0$ transgenic plants were prepared by heating 10–30 whole seeds from individual plants at 85° C. for 90 min in 1 ml of 0.1 M sodium methoxide. Methyl esters were extracted with hexane and analysed by gas liquid chromatography through a 50 m×0.32 mm CP-Wax58-CB fused silica column (Chrompack).

REFERENCES

Badami, R. C., and Patil, K. B. (1981). Strucure and occurrence of unusual fatty acids in minor seed oils. Progress in Lipid Research, 19, 119–53.

Banas, A., Bafor, M., Wiberg, E., Lenman, M., Ståhl, U. and Stymne, S. (1997) Biosynthesis of an acetylenic fatty acid in microsomal preparations from developing seeds of *Crepis alpina*. In: Williams, J. P., Mobasher, K. U., Lem, N. W. (eds) Physiology, biochemistry and molecular biology of plant lipids. Kluwer Academic Publisher, Dordrecht. In-press Becker, D., Kemper, E., Schell, J., Masterson, R., Plant Mol. Biol. 20, 1195, 1992

Birnboim, H. C., and Doly, J. (1979) A rapid alkaline extraction procedure for screening recombinant plasmid DNA. Nucleic Acids Res. 7, 1513–1523

Diedrich, M. & Henschel, K. P. (1991) The natural occurence of unusual fatty acids: Part 3. Acetylenic fatty acids. Nahrung 35, 193–202

Elble, R. (1992) A simple and efficient procedure for transformation of yeasts. Biotechniques 13, 18–20

Haigh, W. G. &, James, A. T. Biochim. Biophys. Acta 137, 391–392

Hirsinger, F. (1989). New annual oil crops. In Oil crops of the world, (eds. G. Röbbelen, R. K. Downey and A. Ashri), pp.518–532. Mc-Graw-Hill Inc.

Kohn, G., Hartmann, E., Stymne, S. & Beutelmann, P. (1994) Biosynthesis of acetylenic acids in the moss Ceratodon purpureus. J. Plant Physiol. 144, 265–271

Langridge, J., Langridge, P and Bergquist P. L. (1980) Extraction of nucleic acids from agarose gels. Anal. Biochem. 103, 264–271

Nilsson, R. and Liljenberg, C. (1991) The determination of double bond positions in polyunsaturated fatty acids—Gaschromatography/mass spectrometry of the diethylamide derivative. Phytochemical analysis 2, 253–259

Shanklin, J., Whittle, E. & Fox, B. G. (1994) Eight histidine residues are catalytically essential in membrane-associated iron enzyme, stearoyl-CoA desaturase and are conserved in alkane hydroxylase and xylene monoxygenase. Biochemistry 33, 12787–12794.

Stymne, S. & Lenman, M. (1996) Novel plant enzyme and use thereof. Swedish patent application no. 9601236-4, 96-03-29.

Stålberg, K., Ellerström, M., Josefsson, L., Rask, L., Plant Molecular Biology 23, 671(1993)

Valvekens, D., Van Montagu M., and Van Lusbettens, Proc. Natl. Acad. Sci. U.S.A. 85, 5536 (1988)

Vernet, T., Dignard, D. and Thomas, D. Y. (1987) A family of yeast expression vectors containing the phafe f1 intergenic region. Gene 52, 225–233

Wieland, B., Feil, C., Gloria-Maercker, E., Thumm, G., Lechner, M., Bravo, J. M., Poralla, K. & Goetz, F. (1994) Genetic and biochemical analysis of the biosynthesis of the yellow carotenoid 4,4'-diaponeurosporene of Staphylococcus aureus. J. Bacteriol. 176, 7719–7726.

van de Loo, F. J., Broun, P., Turner, S. & Somerville, C. (1995) An oleate D12-hydroxylase from Ricinus communis L. is a fatty acid acyl desaturase homolog. Proc. Natl. Acad. Sci. USA 95, 6743–6747.

van de Loo, F. J., Fox, G. & Somerville, C. (1993) Unusual fatty acids. In: T. S. Moore Jr (ed.) Lipid Metabolism in Plants. CRC Press, Boca Raton, page 105.

What is claimed is:

1. An isolated DNA molecule encoding *Crepis alpina* delta 12 acetylenase, comprising the nucleotide sequence of SEQ ID NO:1.

2. An organism transformed with the DNA molecule according to claim 1, wherein the organism is selected from the group consisting of oil crops, oleaginous yeasts and molds, and wherein said DNA molecule is operably linked to a heterologous promoter.

3. The organism according to claim 2, which is an organism accumulating acetylenic fatty acid compounds.

4. The organism according to claim 2, which is an organism that accumulates oil.

5. A method of obtaining acetylenic compounds, comprising accumulation of acetylenic fatty acid compounds in the organism of claim 3.

6. A method of obtaining oils, comprising accumulation of oils in the organism of claim 4.

7. The organism according to claim 2, wherein the acetylenic fatty acid compounds consist of an acyl chain having two adjacent carbon atoms linked by an acetylenic or triple bond.

8. The method according to claim 5, wherein the acetylenic fatty acid compounds consist of an acyl chain having two adjacent carbon atoms linked by an acetylenic or triple bond.

* * * * *

SEQUENCE LISTING

<160> NUMBER OF SEQ ID NOS: 26

<210> SEQ ID NO 1
<211> LENGTH: 1128
<212> TYPE: DNA
<213> ORGANISM: Crepis alpina
<220> FEATURE:
<221> NAME/KEY: CDS
<222> LOCATION: (1)..(1125)

<400> SEQUENCE: 1

```
atg ggt ggc ggt ggc cgt ggt cgg act tcg caa aaa ccc ctc atg gaa        48
Met Gly Gly Gly Gly Arg Gly Arg Thr Ser Gln Lys Pro Leu Met Glu
 1               5                  10                  15 cgt gtc tca gtt gat cca ccc ttc acc gtg agt gat ctc aag caa gca        96
Arg Val Ser Val Asp Pro Pro Phe Thr Val Ser Asp Leu Lys Gln Ala
                20                  25                  30 atc cct ccc cat tgc ttc aag cga tct gta atc cgt tcc tct tac tac       144
Ile Pro Pro His Cys Phe Lys Arg Ser Val Ile Arg Ser Ser Tyr Tyr
            35                  40                  45 ata gtc cac gat gct att atc gcc tac atc ttc tac ttc ctt gcc gac       192
Ile Val His Asp Ala Ile Ile Ala Tyr Ile Phe Tyr Phe Leu Ala Asp
        50                  55                  60 aaa tac att ccg att ctc cct gcc cct cta gcc tac ctc gct tgg ccc       240
Lys Tyr Ile Pro Ile Leu Pro Ala Pro Leu Ala Tyr Leu Ala Trp Pro
 65                  70                  75                  80 ctt tac tgg ttc tgt caa gct agc atc ctc acc ggc tta tgg gtc atc       288
Leu Tyr Trp Phe Cys Gln Ala Ser Ile Leu Thr Gly Leu Trp Val Ile
                85                  90                  95 ggt cac gaa tgc ggt cac cat gcc ttc agc gac tac cag tgg gtt gac       336
```

```
                                                                            -continued Gly His Glu Cys Gly His His Ala Phe Ser Asp Tyr Gln Trp Val Asp
             100                 105                 110 gac act gtg ggc ttc atc ctc cac tcg ttt ctc atg acc ccg tat ttc      384
Asp Thr Val Gly Phe Ile Leu His Ser Phe Leu Met Thr Pro Tyr Phe
         115                 120                 125 tcc tgg aaa tac agc cac cgg aac cac cat gcc aac aca aat tcg ctt      432
Ser Trp Lys Tyr Ser His Arg Asn His His Ala Asn Thr Asn Ser Leu
     130                 135                 140 gac aac gat gaa gtt tac atc ccc aaa agc aag gcc aaa gtc gcg ctt      480
Asp Asn Asp Glu Val Tyr Ile Pro Lys Ser Lys Ala Lys Val Ala Leu
145                 150                 155                 160 tac tat aaa gtt ctc aac cac cca cct ggc cga ctg ttg att atg ttc      528
Tyr Tyr Lys Val Leu Asn His Pro Pro Gly Arg Leu Leu Ile Met Phe
                 165                 170                 175 atc acc ttc acc cta ggc ttc cct cta tac ctc ttt acc aat att tcc      576
Ile Thr Phe Thr Leu Gly Phe Pro Leu Tyr Leu Phe Thr Asn Ile Ser
             180                 185                 190 ggc aag aag tat gaa agg ttt gcc aac cat ttc gac ccc atg agt ccg      624
Gly Lys Lys Tyr Glu Arg Phe Ala Asn His Phe Asp Pro Met Ser Pro
         195                 200                 205 att ttc aaa gag cgt gag cgg ttt cag gtc ttg cta tcg gat ctt ggc      672
Ile Phe Lys Glu Arg Glu Arg Phe Gln Val Leu Leu Ser Asp Leu Gly
     210                 215                 220 ctt ctt gct gtg ctt tac gga gtt aaa ctt gcg gta gca gcg aaa ggc      720
Leu Leu Ala Val Leu Tyr Gly Val Lys Leu Ala Val Ala Ala Lys Gly
225                 230                 235                 240 gcc gcc tgg gtg acg tgc att tac gga att cca gtt tta ggc gtg ttt      768
Ala Ala Trp Val Thr Cys Ile Tyr Gly Ile Pro Val Leu Gly Val Phe
                 245                 250                 255 atc ttt ttc gat atc atc acc tac ttg cac cac acc cat ctg tcg ttg      816
Ile Phe Phe Asp Ile Ile Thr Tyr Leu His His Thr His Leu Ser Leu
             260                 265                 270 cct cat tat gat tca tct gaa tgg aac tgg ctc aga ggg gct ttg tca      864
Pro His Tyr Asp Ser Ser Glu Trp Asn Trp Leu Arg Gly Ala Leu Ser
         275                 280                 285 aca atc gat agg gac ttt ggg ttc ctg aat agt gtg ctc cat gat gtt      912
Thr Ile Asp Arg Asp Phe Gly Phe Leu Asn Ser Val Leu His Asp Val
     290                 295                 300 aca cac act cac gtt atg cat cat ctg ttt tca tac att cca cac tat      960
Thr His Thr His Val Met His His Leu Phe Ser Tyr Ile Pro His Tyr
305                 310                 315                 320 cat gcg aag gag gca agg gat gca atc aac aca gtc ttg ggc gac ttt     1008
His Ala Lys Glu Ala Arg Asp Ala Ile Asn Thr Val Leu Gly Asp Phe
                 325                 330                 335 tat aag atc gat agg act cca att ctg aaa gca atg tgg aga gag gcc     1056
Tyr Lys Ile Asp Arg Thr Pro Ile Leu Lys Ala Met Trp Arg Glu Ala
             340                 345                 350 aag gaa tgc atc ttc atc gag cct gaa aaa ggt agg gag tcc aag ggt     1104
Lys Glu Cys Ile Phe Ile Glu Pro Glu Lys Gly Arg Glu Ser Lys Gly
         355                 360                 365 gta tat tgg tac aat aaa ttc tga                                     1128
Val Tyr Trp Tyr Asn Lys Phe
     370                 375

<210> SEQ ID NO 2
<211> LENGTH: 375
<212> TYPE: PRT
<213> ORGANISM: Crepis alpina

<400> SEQUENCE: 2
```

Met Gly Gly Gly Arg Gly Arg Thr Ser Gln Lys Pro Leu Met Glu
1               5                   10                  15

Arg Val Ser Val Asp Pro Pro Phe Thr Val Ser Asp Leu Lys Gln Ala
            20                  25                  30

Ile Pro Pro His Cys Phe Lys Arg Ser Val Ile Arg Ser Ser Tyr Tyr
                35                  40                  45

Ile Val His Asp Ala Ile Ile Ala Tyr Ile Phe Tyr Phe Leu Ala Asp
            50                  55                  60

Lys Tyr Ile Pro Ile Leu Pro Ala Pro Leu Ala Tyr Leu Ala Trp Pro
65                  70                  75                  80

Leu Tyr Trp Phe Cys Gln Ala Ser Ile Leu Thr Gly Leu Trp Val Ile
                85                  90                  95

Gly His Glu Cys Gly His His Ala Phe Ser Asp Tyr Gln Trp Val Asp
            100                 105                 110

Asp Thr Val Gly Phe Ile Leu His Ser Phe Leu Met Thr Pro Tyr Phe
            115                 120                 125

Ser Trp Lys Tyr Ser His Arg Asn His His Ala Asn Thr Asn Ser Leu
    130                 135                 140

Asp Asn Asp Glu Val Tyr Ile Pro Lys Ser Lys Ala Lys Val Ala Leu
145                 150                 155                 160

Tyr Tyr Lys Val Leu Asn His Pro Pro Gly Arg Leu Leu Ile Met Phe
                165                 170                 175

Ile Thr Phe Thr Leu Gly Phe Pro Leu Tyr Leu Phe Thr Asn Ile Ser
            180                 185                 190

Gly Lys Lys Tyr Glu Arg Phe Ala Asn His Phe Asp Pro Met Ser Pro
    195                 200                 205

Ile Phe Lys Glu Arg Glu Arg Phe Gln Val Leu Leu Ser Asp Leu Gly
    210                 215                 220

Leu Leu Ala Val Leu Tyr Gly Val Lys Leu Ala Val Ala Ala Lys Gly
225                 230                 235                 240

Ala Ala Trp Val Thr Cys Ile Tyr Gly Ile Pro Val Leu Gly Val Phe
                245                 250                 255

Ile Phe Phe Asp Ile Ile Thr Tyr Leu His His Thr His Leu Ser Leu
            260                 265                 270

Pro His Tyr Asp Ser Ser Glu Trp Asn Trp Leu Arg Gly Ala Leu Ser
    275                 280                 285

Thr Ile Asp Arg Asp Phe Gly Phe Leu Asn Ser Val Leu His Asp Val
    290                 295                 300

Thr His Thr His Val Met His His Leu Phe Ser Tyr Ile Pro His Tyr
305                 310                 315                 320

His Ala Lys Glu Ala Arg Asp Ala Ile Asn Thr Val Leu Gly Asp Phe
                325                 330                 335

Tyr Lys Ile Asp Arg Thr Pro Ile Leu Lys Ala Met Trp Arg Glu Ala
            340                 345                 350

Lys Glu Cys Ile Phe Ile Glu Pro Glu Lys Gly Arg Glu Ser Lys Gly
            355                 360                 365

Val Tyr Trp Tyr Asn Lys Phe
    370                 375

<210> SEQ ID NO 3
<211> LENGTH: 443
<212> TYPE: PRT
<213> ORGANISM: Brassica napus

<400> SEQUENCE: 3

-continued

```
Met Ala Ser Arg Ile Ala Asp Ser Leu Phe Ala Phe Thr Gly Pro Gln
 1               5                  10                  15

Gln Cys Leu Pro Arg Ala Pro Lys Leu Ala Ser Ala Arg Leu Ser Pro
             20                  25                  30

Gly Val Tyr Ala Val Arg Pro Ile Asp Leu Leu Lys Gly Thr Arg
         35                  40                  45

Arg Thr Phe Leu Val Pro Ala Lys Lys Arg Ile Gly Cys Ile Lys Ala
     50                  55                  60

Val Phe Val Pro Val Ala Pro Ser Ala Asp Asn Ala Glu Asp Arg
 65              70                  75                  80

Glu Gln Leu Ala Glu Ser Tyr Gly Phe Lys Gln Ile Gly Gln Asp Leu
             85                  90                  95

Pro Asp Asn Val Thr Leu Lys Asp Ile Met Asp Thr Leu Pro Lys Glu
                100                 105                 110

Val Phe Glu Ile Asp Asp Val Lys Ala Trp Lys Ser Val Leu Ile Ser
         115                 120                 125

Val Thr Ser Tyr Ala Leu Gly Leu Phe Met Ile Ala Lys Ala Pro Trp
     130                 135                 140

Tyr Leu Leu Pro Leu Ala Trp Ala Trp Thr Gly Thr Ala Val Thr Gly
145                 150                 155                 160

Phe Phe Val Ile Gly His Asp Cys Ala His Lys Ser Phe Ser Lys Asn
                165                 170                 175

Lys Leu Val Glu Asp Ile Val Gly Thr Leu Ala Phe Leu Pro Leu Val
             180                 185                 190

Tyr Pro Tyr Glu Pro Trp Arg Phe Lys His Asp Arg His His Ala Lys
         195                 200                 205

Thr Asn Met Leu Val His Asp Thr Ala Trp Gln Pro Val Pro Pro Glu
     210                 215                 220

Glu Phe Asp Ser Ser Pro Val Leu Arg Lys Ala Ile Ile Phe Gly Tyr
225                 230                 235                 240

Gly Pro Ile Arg Pro Trp Leu Ser Ile Ala His Trp Val Asn Trp His
                245                 250                 255

Phe Asn Leu Arg Lys Phe Arg Pro Ser Glu Val Asn Arg Val Lys Ile
             260                 265                 270

Ser Leu Ala Cys Val Phe Ala Phe Met Ala Val Gly Trp Pro Leu Ile
         275                 280                 285

Ile Tyr Lys Val Gly Val Leu Gly Trp Val Lys Phe Trp Leu Met Pro
     290                 295                 300

Trp Leu Gly Tyr His Phe Trp Met Ser Thr Phe Thr Met Val His His
305                 310                 315                 320

Thr Ala Pro His Ile Pro Phe Lys Pro Ala Asp Glu Trp Asn Ala Ala
                325                 330                 335

Gln Ala Gln Leu Asn Gly Thr Val His Cys Asp Tyr Pro Ser Trp Ile
             340                 345                 350

Glu Ile Leu Cys His Asp Ile Asn Val His Ile Pro His His Ile Ser
         355                 360                 365

Pro Arg Ile Pro Ser Tyr Asn Leu Arg Ala Ala His Gln Ser Ile Gln
     370                 375                 380

Glu Asn Trp Gly Lys Tyr Thr Asn Leu Ala Thr Trp Asn Trp Arg Leu
385                 390                 395                 400

Met Lys Thr Ile Met Thr Val Cys His Val Tyr Asp Lys Glu Glu Asn
                405                 410                 415
```

```
Tyr Ile Pro Phe Asp Arg Leu Ala Pro Glu Glu Ser Gln Pro Ile Thr
            420                 425                 430
Phe Leu Lys Lys Ala Met Pro Asp Tyr Ala Ala
        435                 440

<210> SEQ ID NO 4
<211> LENGTH: 424
<212> TYPE: PRT
<213> ORGANISM: Glycine max

<400> SEQUENCE: 4

Met Ala Cys Thr Leu Ala Asp Ser Leu Leu Phe Lys Gly Ser Tyr
 1               5                  10                  15
Gln Lys Pro Val Leu Arg Arg Asp Ile Ala Ala Arg Tyr Ser Pro Gly
            20                  25                  30
Ile Phe Ser Leu Asn Ser Asn Gly Leu Ile Gln Lys Arg Phe Arg Arg
        35                  40                  45
Gln Arg Asn Phe Val Thr Arg Asn Lys Val Thr Val Ile His Ala Val
    50                  55                  60
Ala Ile Pro Val Gln Pro Ala Pro Val Glu Ser Ala Glu Tyr Arg Lys
65                  70                  75                  80
Gln Leu Ala Glu Asp Tyr Gly Phe Arg Gln Val Gly Glu Pro Leu Ser
                85                  90                  95
Asp Asp Val Thr Leu Lys Asp Val Ile Asn Pro Leu Pro Lys Glu Val
            100                 105                 110
Phe Glu Ile Asp Asp Val Lys Ala Trp Lys Ser Val Leu Ile Ser Val
        115                 120                 125
Thr Ser Tyr Ala Leu Gly Leu Phe Met Ile Ser Lys Ala Pro Trp Tyr
    130                 135                 140
Leu Leu Pro Leu Ala Trp Val Trp Thr Gly Thr Ala Ile Thr Gly Phe
145                 150                 155                 160
Phe Val Ile Gly His Asp Cys Ala His Arg Ser Phe Ser Ser Asn Lys
                165                 170                 175
Leu Val Glu Asp Ile Val Gly Thr Leu Ala Phe Met Pro Leu Ile Tyr
            180                 185                 190
Pro Tyr Glu Pro Trp Arg Phe Lys His Asp Arg His His Ala Lys Thr
        195                 200                 205
Asn Met Leu Arg Glu Asp Thr Ala Trp His Pro Val Trp Lys Asp Glu
    210                 215                 220
Phe Glu Ser Thr Pro Leu Leu Arg Lys Ala Ile Ile Tyr Gly Tyr Gly
225                 230                 235                 240
Pro Phe Arg Cys Trp Met Ser Ile Ala His Trp Leu Met Trp His Phe
                245                 250                 255
Asp Leu Lys Lys Phe Arg Pro Ser Glu Val Pro Arg Val Lys Ile Ser
            260                 265                 270
Leu Ala Cys Val Phe Ala Phe Ile Ala Ile Gly Trp Pro Leu Ile Ile
        275                 280                 285
Tyr Lys Thr Gly Ile Met Gly Trp Ile Lys Phe Trp Leu Met Pro Trp
    290                 295                 300
Leu Gly Tyr His Phe Trp Met Ser Thr Phe Thr Met Val His His Thr
305                 310                 315                 320
Ala Pro Tyr Ile Pro Phe Lys Tyr Ser Glu Glu Trp Asn Arg Ala Gln
                325                 330                 335
Ala Gln Leu Asn Gly Thr Val His Cys Asp Tyr Pro Lys Trp Ile Glu
            340                 345                 350
```

-continued

```
Ile Leu Cys His Asp Ile Asn Val His Ile Pro His His Ile Ser Pro
            355                 360                 365
Arg Ile Pro Ser Tyr Asn Leu Arg Ala Ala His Lys Ser Leu Gln Glu
        370                 375                 380
Asn Trp Gly Gln Tyr Leu Asn Glu Ala Ser Trp Asn Trp Arg Leu Met
385                 390                 395                 400
Lys Thr Ile Met Thr Val Cys Gln Val Tyr Asp Lys Glu Lys Ser Leu
                405                 410                 415
Cys Cys Leu Arg Arg Thr Cys Pro
            420
```

<210> SEQ ID NO 5
<211> LENGTH: 446
<212> TYPE: PRT
<213> ORGANISM: Arabidopsis thaliana

<400> SEQUENCE: 5

```
Met Ala Asn Leu Val Leu Ser Glu Cys Gly Ile Arg Pro Leu Pro Arg
  1               5                  10                  15
Ile Tyr Thr Thr Pro Arg Ser Asn Phe Leu Ser Asn Asn Lys Phe
             20                  25                  30
Arg Pro Ser Leu Ser Ser Ser Tyr Lys Thr Ser Ser Ser Pro Leu
         35                  40                  45
Ser Phe Gly Leu Asn Ser Arg Asp Gly Phe Thr Arg Asn Trp Ala Leu
     50                  55                  60
Asn Val Ser Thr Pro Leu Thr Thr Pro Ile Phe Glu Glu Ser Pro Leu
 65                  70                  75                  80
Glu Glu Asp Asn Lys Gln Arg Phe Asp Pro Gly Ala Pro Pro Phe
                 85                  90                  95
Asn Leu Ala Asp Ile Arg Ala Ala Ile Pro Lys His Cys Trp Val Lys
             100                 105                 110
Asn Pro Trp Lys Ser Leu Ser Tyr Val Val Arg Asp Val Ala Ile Val
         115                 120                 125
Phe Ala Leu Ala Ala Gly Ala Ala Tyr Leu Asn Asn Trp Ile Val Trp
 130                 135                 140
Pro Leu Tyr Trp Leu Ala Gln Gly Thr Met Phe Trp Ala Leu Phe Val
145                 150                 155                 160
Leu Gly His Asp Cys Gly His Gly Ser Phe Ser Asn Asp Pro Lys Leu
                165                 170                 175
Asn Ser Val Val Gly His Leu Leu His Ser Ser Ile Leu Val Pro Tyr
            180                 185                 190
His Gly Trp Arg Ile Ser His Arg Thr His Gln Asn His Gly His
        195                 200                 205
Val Glu Asn Asp Glu Ser Trp His Pro Met Ser Glu Lys Ile Tyr Asn
    210                 215                 220
Thr Leu Asp Lys Pro Thr Arg Phe Phe Arg Phe Thr Leu Pro Leu Val
225                 230                 235                 240
Met Leu Ala Tyr Pro Phe Tyr Leu Trp Ala Arg Ser Pro Gly Lys Lys
                245                 250                 255
Gly Ser His Tyr His Pro Asp Ser Asp Leu Phe Leu Pro Lys Glu Arg
            260                 265                 270
Lys Asp Val Leu Thr Ser Thr Ala Cys Trp Thr Ala Met Ala Ala Leu
        275                 280                 285
Leu Val Cys Leu Asn Phe Thr Ile Gly Pro Ile Gln Met Leu Lys Leu
```

```
            290                 295                 300
Tyr Gly Ile Pro Tyr Trp Ile Asn Val Met Trp Leu Asp Phe Val Thr
305                 310                 315                 320

Tyr Leu His His His Gly His Glu Asp Lys Leu Pro Trp Tyr Arg Gly
                    325                 330                 335

Lys Glu Trp Ser Tyr Leu Arg Gly Leu Thr Thr Leu Asp Arg Asp
                340                 345                 350

Tyr Gly Leu Ile Asn Asn Ile His His Asp Ile Gly Thr His Val Ile
                355                 360                 365

His His Leu Phe Pro Gln Ile Pro His His Leu Val Glu Ala Thr
        370                 375                 380

Glu Ala Ala Lys Pro Val Leu Gly Lys Tyr Tyr Arg Glu Pro Asp Lys
385                 390                 395                 400

Ser Gly Pro Leu Pro Leu His Leu Leu Glu Ile Leu Ala Lys Ser Ile
                405                 410                 415

Lys Glu Asp His Tyr Val Ser Asp Glu Gly Val Val Tyr Tyr Lys
                420                 425                 430

Ala Asp Pro Asn Leu Tyr Gly Glu Val Lys Val Arg Ala Asp
                435                 440                 445

<210> SEQ ID NO 6
<211> LENGTH: 329
<212> TYPE: PRT
<213> ORGANISM: Brassica napus

<400> SEQUENCE: 6

Met Ser Tyr Val Val Arg Glu Leu Ala Ile Val Phe Ala Leu Ala Ala
1               5                   10                  15

Gly Ala Ala Tyr Leu Asn Asn Trp Leu Val Trp Pro Leu Tyr Trp Ile
                20                  25                  30

Ala Gln Gly Thr Met Phe Trp Ala Leu Phe Val Leu Gly His Asp Cys
                35                  40                  45

Gly His Gly Ser Phe Ser Asn Asp Pro Arg Leu Asn Ser Val Val Gly
            50                  55                  60

His Leu Leu His Ser Ser Ile Leu Val Pro Tyr His Gly Trp Arg Ile
65                  70                  75                  80

Ser His Arg Thr His His Gln Asn His Gly His Val Glu Asn Asp Glu
                85                  90                  95

Ser Trp His Pro Met Ser Glu Lys Ile Tyr Lys Ser Leu Asp Lys Pro
                100                 105                 110

Thr Arg Phe Phe Arg Phe Thr Leu Pro Leu Val Met Leu Ala Tyr Pro
            115                 120                 125

Phe Tyr Leu Trp Ala Arg Ser Pro Gly Lys Lys Gly Ser His Tyr His
        130                 135                 140

Pro Asp Ser Asp Leu Phe Leu Pro Lys Glu Arg Asn Asp Val Leu Thr
145                 150                 155                 160

Ser Thr Ala Cys Trp Thr Ala Met Ala Val Leu Leu Val Cys Leu Asn
                165                 170                 175

Phe Val Met Gly Pro Met Gln Met Leu Lys Leu Tyr Val Ile Pro Tyr
                180                 185                 190

Trp Ile Asn Val Met Trp Leu Asp Phe Val Thr Tyr Leu His His His
            195                 200                 205

Gly His Glu Asp Lys Leu Pro Trp Tyr Arg Gly Lys Glu Trp Ser Tyr
        210                 215                 220
```

```
Leu Arg Gly Gly Leu Thr Thr Leu Asp Arg Asp Tyr Gly Leu Ile Asn
225                 230                 235                 240

Asn Ile His His Asp Ile Gly Thr His Val Ile His His Leu Phe Pro
                245                 250                 255

Gln Ile Pro His Tyr His Leu Val Glu Ala Thr Glu Ala Ala Lys Pro
                260                 265                 270

Val Leu Gly Lys Tyr Tyr Arg Glu Pro Asp Lys Ser Gly Pro Leu Pro
                275                 280                 285

Leu His Leu Leu Gly Ile Leu Ala Lys Ser Ile Lys Glu Asp His Phe
                290                 295                 300

Val Ser Asp Glu Gly Asp Val Val Tyr Tyr Glu Ala Asp Pro Asn Leu
305                 310                 315                 320

Tyr Gly Glu Ile Lys Val Thr Ala Glu
                325
```

<210> SEQ ID NO 7
<211> LENGTH: 460
<212> TYPE: PRT
<213> ORGANISM: Ricinus communis

<400> SEQUENCE: 7

```
Met Ala Ala Gly Trp Val Leu Ser Glu Cys Gly Leu Arg Pro Leu Pro
1               5                   10                  15

Arg Ile Tyr Ser Arg Pro Arg Ile Gly Phe Thr Ser Lys Thr Thr Asn
                20                  25                  30

Leu Leu Lys Leu Arg Glu Leu Pro Asp Ser Lys Ser Tyr Asn Leu Cys
                35                  40                  45

Ser Ser Phe Lys Val Ser Ser Trp Ser Asn Ser Lys Gln Ser Asn Trp
                50                  55                  60

Ala Leu Asn Val Ala Val Pro Val Asn Val Ser Thr Val Ser Gly Glu
65                  70                  75                  80

Asp Asp Arg Glu Arg Glu Phe Asn Gly Ile Val Asn Val Asp Glu
                85                  90                  95

Gly Lys Gly Glu Phe Phe Asp Ala Gly Ala Pro Pro Phe Thr Leu
                100                 105                 110

Ala Asp Ile Arg Ala Ala Ile Pro Lys His Cys Trp Val Lys Asn Pro
                115                 120                 125

Trp Arg Ser Met Ser Tyr Val Leu Arg Asp Val Val Val Phe Gly
                130                 135                 140

Leu Ala Ala Val Ala Ala Tyr Phe Asn Asn Trp Val Ala Trp Pro Leu
145                 150                 155                 160

Tyr Trp Phe Cys Gln Gly Thr Met Phe Trp Ala Leu Phe Val Leu Gly
                165                 170                 175

His Asp Cys Gly His Gly Ser Phe Ser Asn Asn Pro Lys Leu Asn Ser
                180                 185                 190

Val Val Gly His Leu Leu His Ser Ser Ile Leu Val Pro Tyr His Gly
                195                 200                 205

Trp Arg Ile Ser His Arg Thr His His Gln Asn His Gly His Val Glu
                210                 215                 220

Asn Asp Glu Ser Trp His Pro Leu Ser Glu Lys Ile Phe Lys Ser Leu
225                 230                 235                 240

Asp Asn Val Thr Lys Thr Leu Arg Phe Ser Leu Pro Phe Pro Met Leu
                245                 250                 255

Ala Tyr Pro Phe Tyr Leu Trp Ser Arg Ser Pro Gly Lys Lys Gly Ser
                260                 265                 270
```

```
His Phe His Pro Asp Ser Gly Leu Phe Val Pro Lys Glu Arg Lys Asp
            275                 280                 285
Ile Ile Thr Ser Thr Ala Cys Trp Thr Ala Met Ala Ala Leu Leu Val
    290                 295                 300
Tyr Leu Asn Phe Ser Met Gly Pro Val Gln Met Leu Lys Leu Tyr Gly
305                 310                 315                 320
Ile Pro Tyr Trp Ile Phe Val Met Trp Leu Asp Phe Val Thr Tyr Leu
                325                 330                 335
His His His Gly His Glu Asp Lys Leu Pro Trp Tyr Arg Gly Lys Ala
            340                 345                 350
Trp Ser Tyr Leu Arg Gly Gly Leu Thr Thr Leu Asp Arg Asp Tyr Gly
            355                 360                 365
Trp Ile Asn Asn Ile His His Asp Ile Gly Thr His Val Ile His His
    370                 375                 380
Leu Phe Pro Gln Ile Pro His Tyr His Leu Val Glu Ala Thr Glu Ala
385                 390                 395                 400
Ala Lys Pro Val Met Gly Lys Tyr Tyr Arg Glu Pro Lys Lys Ser Gly
                405                 410                 415
Pro Leu Pro Leu His Leu Leu Gly Ser Leu Val Arg Ser Met Lys Glu
            420                 425                 430
Asp His Tyr Val Ser Asp Thr Gly Asp Val Val Tyr Tyr Gln Lys Asp
            435                 440                 445
Pro Lys Leu Ser Gly Ile Gly Gly Glu Lys Thr Glu
    450                 455                 460

<210> SEQ ID NO 8
<211> LENGTH: 447
<212> TYPE: PRT
<213> ORGANISM: oriental sesame

<400> SEQUENCE: 8

Met Ala Ser Trp Val Leu Ser Glu Cys Gly Leu Arg Pro Leu Pro Arg
1               5                   10                  15
Val Tyr Pro Lys Pro Arg Thr Gly His Pro Leu Leu Asn Ser Asn Pro
            20                  25                  30
Thr Lys Leu Arg Phe Ser Arg Thr Asp Leu Gly Asn Gly Ser Ser Phe
        35                  40                  45
Cys Leu Ser Ser Gly Ile Leu Arg Glu Lys Asn Trp Ala Leu Arg Val
    50                  55                  60
Ser Ala Pro Leu Arg Val Leu Gln Val Glu Glu Glu Glu Asn Lys
65                  70                  75                  80
Glu Gly Glu Arg Val Ile Asn Gly Gly Glu Glu Phe Asp Pro Gly Ala
                85                  90                  95
Pro Pro Pro Phe Lys Leu Ser Asp Ile Arg Glu Ala Ile Pro Lys His
            100                 105                 110
Cys Trp Val Lys Asp Pro Trp Arg Ser Met Gly Tyr Val Val Arg Asp
        115                 120                 125
Val Ala Val Val Phe Gly Leu Ala Ala Val Ala Ala Tyr Phe Asn Asn
    130                 135                 140
Trp Val Val Trp Pro Leu Tyr Trp Phe Ala Gln Ser Thr Met Phe Trp
145                 150                 155                 160
Ala Leu Phe Val Leu Gly His Asp Cys Gly His Gly Ser Phe Ser Asn
                165                 170                 175
Asp Pro Lys Leu Asn Ser Val Val Gly His Ile Leu His Ser Ser Ile
```

-continued

```
            180             185             190
Leu Val Pro Tyr His Gly Trp Arg Ile Ser His Arg Thr His His Gln
        195             200             205
Asn His Gly His Val Glu Asn Asp Glu Ser Trp His Pro Leu Ser Glu
    210             215             220
Lys Ile Tyr Lys Asn Leu Asp Thr Ala Thr Lys Lys Leu Arg Phe Thr
225             230             235             240
Leu Pro Phe Pro Leu Leu Ala Tyr Pro Ile Tyr Leu Trp Ser Arg Ser
            245             250             255
Pro Gly Lys Gln Gly Ser His Phe His Pro Asp Ser Asp Leu Phe Val
        260             265             270
Pro Asn Glu Lys Lys Asp Val Ile Thr Ser Thr Val Cys Trp Thr Ala
    275             280             285
Met Leu Ala Leu Leu Val Gly Leu Ser Phe Val Ile Gly Pro Val Gln
    290             295             300
Leu Leu Lys Leu Tyr Gly Ile Pro Tyr Leu Gly Asn Val Met Trp Leu
305             310             315             320
Asp Leu Val Thr Tyr Leu His His His Gly His Glu Asp Lys Leu Pro
            325             330             335
Trp Tyr Arg Gly Lys Glu Trp Ser Tyr Leu Arg Gly Gly Leu Thr Thr
        340             345             350
Leu Asp Arg Asp Tyr Gly Trp Ile Asn Asn Ile His His Asp Ile Gly
        355             360             365
Thr His Val Ile His His Leu Phe Pro Gln Ile Pro His Tyr His Leu
    370             375             380
Ile Glu Ala Thr Glu Ala Ala Lys Pro Val Leu Gly Lys Tyr Tyr Arg
385             390             395             400
Glu Pro Lys Lys Ser Ala Pro Leu Pro Phe His Leu Leu Gly Asp Leu
            405             410             415
Thr Arg Ser Leu Lys Arg Asp His Tyr Val Ser Asp Val Gly Asp Val
        420             425             430
Val Tyr Tyr Gln Thr Asp Pro Gln Leu Thr Gly Ala Glu Lys Ser
        435             440             445

<210> SEQ ID NO 9
<211> LENGTH: 436
<212> TYPE: PRT
<213> ORGANISM: Limnanthes douglasii

<400> SEQUENCE: 9

Met Ala Ser Trp Val Leu Ser Gln Tyr Ala Leu Asn Pro Leu Pro His
  1               5                  10                  15
Ile Phe Arg Thr Pro Arg Thr Ser Ile Thr Ser His Lys Leu Thr Val
                 20                  25                  30
Ser His Thr Asn Asn Arg Ala Thr Pro Asp Leu Thr Lys Leu Ser Leu
             35                  40                  45
Ile Lys Phe Arg Glu Arg Lys Leu Gly Leu Arg Val Ser Ala Pro Phe
         50                  55                  60
Gln Ile Ala Ser Thr Thr Pro Glu Glu Asp Glu Val Ala Glu Phe
 65                  70                  75                  80
Asp Pro Gly Ser Pro Pro Phe Lys Leu Ala Asp Ile Arg Ala Ala
                 85                  90                  95
Ile Pro Lys His Cys Trp Val Lys Asn Gln Trp Arg Ser Met Ser Tyr
                100                 105                 110
```

Val Val Arg Asp Val Val Ile Val Leu Gly Leu Ala Ala Ala Val
            115                 120                 125

Ala Ala Asn Ser Trp Ala Val Trp Pro Leu Tyr Trp Val Ala Gln Gly
        130                 135                 140

Thr Met Phe Trp Ala Leu Phe Val Leu Gly His Asp Cys Gly His Gly
145                 150                 155                 160

Ser Phe Ser Asn Asn His Lys Leu Asn Ser Val Val Gly His Leu Leu
                165                 170                 175

His Ser Ser Ile Leu Val Pro Tyr His Gly Trp Arg Ile Arg His Arg
            180                 185                 190

Thr His His Gln Asn His Gly His Val Glu Asn Asp Glu Ser Trp His
        195                 200                 205

Pro Met Ser Glu Lys Leu Phe Arg Ser Leu Asp Lys Ile Ala Leu Thr
    210                 215                 220

Phe Arg Phe Lys Ala Pro Phe Pro Met Leu Ala Tyr Pro Phe Tyr Leu
225                 230                 235                 240

Trp Glu Arg Ser Pro Gly Lys Thr Gly Ser His Tyr His Pro Asp Ser
                245                 250                 255

Asp Leu Phe Val Pro Ser Glu Lys Lys Asp Val Ile Thr Ser Thr Ile
            260                 265                 270

Cys Trp Thr Thr Met Val Gly Leu Leu Ile Gly Leu Ser Phe Val Met
        275                 280                 285

Gly Pro Ile Gln Ile Leu Lys Leu Tyr Val Val Pro Tyr Trp Ile Phe
    290                 295                 300

Val Met Trp Leu Asp Phe Val Thr Tyr Leu His His Gly His Glu
305                 310                 315                 320

Asp Lys Leu Pro Trp Tyr Arg Gly Glu Glu Trp Ser Tyr Leu Arg Gly
                325                 330                 335

Gly Leu Thr Thr Leu Asp Arg Asp Tyr Gly Leu Ile Asn Asn Ile His
            340                 345                 350

His Asp Ile Gly Thr His Val Ile His His Leu Phe Pro Gln Ile Pro
        355                 360                 365

His Tyr His Leu Val Glu Ala Thr Gln Ala Ala Lys Pro Ile Phe Gly
    370                 375                 380

Lys Tyr Tyr Lys Glu Pro Ala Lys Ser Lys Pro Leu Pro Phe His Leu
385                 390                 395                 400

Ile Asp Val Leu Leu Lys Ser Leu Lys Arg Asp His Phe Val Pro Asp
                405                 410                 415

Thr Gly Asp Ile Val Tyr Tyr Gln Ser Asp Pro Gln Ile Ser Gly Ser
            420                 425                 430

Leu Lys Pro Glu
        435

<210> SEQ ID NO 10
<211> LENGTH: 453
<212> TYPE: PRT
<213> ORGANISM: Glycine max

<400> SEQUENCE: 10

Met Ala Thr Trp Tyr His Gln Lys Cys Gly Leu Lys Pro Leu Ala Pro
1               5                   10                  15

Val Ile Pro Arg Pro Arg Thr Gly Ala Ala Leu Ser Ser Thr Ser Arg
                20                  25                  30

Val Glu Phe Leu Asp Thr Asn Lys Val Val Ala Gly Pro Lys Phe Gln
            35                  40                  45

```
Pro Leu Arg Cys Asn Leu Arg Glu Arg Asn Trp Gly Leu Lys Val Ser
    50                      55                  60

Ala Pro Leu Arg Val Ala Ser Ile Glu Glu Gln Lys Ser Val Asp
 65                  70                  75                  80

Leu Thr Asn Gly Thr Asn Gly Val Glu His Glu Lys Leu Pro Glu Phe
                 85                  90                  95

Asp Pro Gly Ala Pro Pro Phe Asn Leu Ala Asp Ile Arg Ala Ala
                100             105                 110

Ile Pro Lys His Cys Trp Val Lys Asp Pro Trp Arg Ser Met Ser Tyr
            115             120             125

Val Val Arg Asp Val Ile Ala Val Phe Gly Leu Ala Ala Ala Ala
    130             135             140

Tyr Leu Asn Asn Trp Leu Val Trp Pro Leu Tyr Trp Ala Ala Gln Gly
145                 150             155                     160

Thr Met Phe Trp Ala Leu Phe Val Leu Gly His Asp Cys Gly His Gly
                165             170                 175

Ser Phe Ser Asn Asn Ser Lys Leu Asn Ser Val Val Gly His Leu Leu
                180             185                 190

His Ser Ser Ile Leu Val Pro Tyr His Gly Trp Arg Ile Ser His Arg
        195                 200             205

Thr His His Gln His His Gly His Ala Glu Asn Asp Glu Ser Trp His
    210                 215             220

Pro Leu Pro Glu Lys Leu Phe Arg Ser Leu Asp Thr Val Thr Arg Met
225             230             235                     240

Leu Arg Phe Thr Ala Pro Phe Pro Leu Leu Ala Phe Pro Val Tyr Leu
                245             250             255

Phe Ser Arg Ser Pro Gly Lys Thr Gly Ser His Phe Asp Pro Ser Ser
                260             265             270

Asp Leu Phe Val Pro Asn Glu Arg Lys Asp Val Ile Thr Ser Thr Ala
        275             280             285

Cys Trp Ala Ala Met Leu Gly Leu Leu Val Gly Leu Gly Phe Val Met
    290             295             300

Gly Pro Ile Gln Leu Leu Lys Leu Tyr Gly Val Pro Tyr Val Ile Phe
305             310             315                     320

Val Met Trp Leu Asp Leu Val Thr Tyr Leu His His Gly His His Glu
                325             330                 335

Asp Lys Leu Pro Trp Tyr Arg Gly Lys Glu Trp Ser Tyr Leu Arg Gly
            340             345             350

Gly Leu Thr Thr Leu Asp Arg Asp Tyr Gly Trp Ile Asn Asn Ile His
            355             360             365

His Asp Ile Gly Thr His Val Ile His His Leu Phe Pro Gln Ile Pro
    370             375             380

His Tyr His Leu Val Glu Ala Thr Glu Ala Ala Lys Pro Val Phe Gly
385                 390             395                     400

Lys Tyr Tyr Arg Glu Pro Lys Lys Ser Ala Ala Pro Leu Pro Phe His
                405             410             415

Leu Ile Gly Glu Ile Ile Arg Ser Phe Lys Thr Asp His Phe Val Ser
            420             425             430

Asp Thr Gly Asp Val Val Tyr Tyr Gln Thr Asp Ser Lys Ile Asn Gly
            435             440             445

Ser Ser Lys Leu Glu
    450
```

```
<210> SEQ ID NO 11
<211> LENGTH: 386
<212> TYPE: PRT
<213> ORGANISM: Arabidopsis thaliana

<400> SEQUENCE: 11

Met Val Val Ala Met Asp Gln Arg Thr Asn Val Asn Gly Asp Pro Gly
 1               5                  10                  15

Ala Gly Asp Arg Lys Lys Glu Glu Arg Phe Asp Pro Ser Ala Gln Pro
                20                  25                  30

Pro Phe Lys Ile Gly Asp Ile Arg Ala Ala Ile Pro Lys His Cys Trp
            35                  40                  45

Val Lys Ser Pro Leu Arg Ser Met Ser Tyr Val Arg Asp Ile Ile
 50                  55                  60

Ala Val Ala Ala Leu Ala Ile Ala Ala Val Tyr Val Asp Ser Trp Phe
 65                  70                  75                  80

Leu Trp Pro Leu Tyr Trp Ala Ala Gln Gly Thr Leu Phe Trp Ala Ile
                85                  90                  95

Phe Val Leu Gly His Asp Cys Gly His Gly Ser Phe Ser Asp Ile Pro
            100                 105                 110

Leu Leu Asn Ser Val Val Gly His Ile Leu His Ser Phe Ile Leu Val
        115                 120                 125

Pro Tyr His Gly Trp Arg Ile Ser His Arg Thr His Gln Asn His
    130                 135                 140

Gly His Val Glu Asn Asp Glu Ser Trp Val Pro Leu Pro Glu Arg Val
145                 150                 155                 160

Tyr Lys Lys Leu Pro His Ser Thr Arg Met Leu Arg Tyr Thr Val Pro
                165                 170                 175

Leu Pro Met Leu Ala Tyr Pro Leu Tyr Leu Cys Tyr Arg Ser Pro Gly
            180                 185                 190

Lys Glu Gly Ser His Phe Asn Pro Tyr Ser Ser Leu Phe Ala Pro Ser
        195                 200                 205

Glu Arg Lys Leu Ile Ala Thr Ser Thr Thr Cys Trp Ser Ile Met Phe
    210                 215                 220

Val Ser Leu Ile Ala Leu Ser Phe Val Phe Gly Pro Leu Ala Val Leu
225                 230                 235                 240

Lys Val Tyr Gly Val Pro Tyr Ile Ile Phe Val Met Trp Leu Asp Ala
                245                 250                 255

Val Thr Tyr Leu His His His Gly His Asp Glu Lys Leu Pro Trp Tyr
            260                 265                 270

Arg Gly Lys Glu Trp Ser Tyr Leu Arg Gly Gly Leu Thr Thr Ile Asp
        275                 280                 285

Arg Asp Tyr Gly Ile Phe Asn Asn Ile His His Asp Ile Gly Thr His
    290                 295                 300

Val Ile His His Leu Phe Pro Gln Ile Pro His Tyr His Leu Val Asp
305                 310                 315                 320

Ala Thr Lys Ala Ala Lys His Val Leu Gly Arg Tyr Tyr Arg Glu Pro
                325                 330                 335

Lys Thr Ser Gly Ala Ile Pro Ile His Leu Val Glu Ser Leu Val Ala
            340                 345                 350

Ser Ile Lys Lys Asp His Tyr Val Ser Asp Thr Gly Asp Ile Val Phe
        355                 360                 365

Tyr Glu Thr Asp Pro Asp Leu Tyr Val Tyr Ala Ser Asp Lys Ser Lys
    370                 375                 380
```

Ile Asn
385

<210> SEQ ID NO 12
<211> LENGTH: 377
<212> TYPE: PRT
<213> ORGANISM: Brassica napus

<400> SEQUENCE: 12

```
Met Val Val Ala Met Asp Gln Arg Ser Asn Ala Asn Gly Asp Glu Arg
 1               5                  10                  15

Phe Asp Pro Ser Ala Gln Pro Pro Phe Lys Ile Gly Asp Ile Arg Ala
                20                  25                  30

Ala Ile Pro Lys His Cys Trp Val Lys Ser Pro Leu Arg Ser Met Ser
            35                  40                  45

Tyr Val Ala Arg Asp Ile Phe Ala Val Val Ala Leu Ala Val Ala Ala
 50                  55                  60

Val Tyr Phe Asp Ser Trp Phe Phe Trp Pro Leu Tyr Trp Ala Ala Gln
 65                  70                  75                  80

Gly Thr Leu Phe Trp Ala Ile Phe Val Leu Gly His Asp Cys Gly His
                85                  90                  95

Gly Ser Phe Ser Asp Ile Pro Leu Leu Asn Thr Ala Val Gly His Ile
            100                 105                 110

Leu His Ser Phe Ile Leu Val Pro Tyr His Gly Trp Arg Ile Ser His
        115                 120                 125

Arg Thr His His Gln Asn His Gly His Val Glu Asn Asp Glu Ser Trp
130                 135                 140

Val Pro Leu Pro Glu Lys Leu Tyr Lys Asn Leu Ser His Ser Thr Arg
145                 150                 155                 160

Met Leu Arg Tyr Thr Val Pro Leu Pro Met Leu Ala Tyr Pro Leu Tyr
                165                 170                 175

Leu Trp Tyr Arg Ser Pro Gly Lys Glu Gly Ser His Tyr Asn Pro Tyr
            180                 185                 190

Ser Ser Leu Phe Ala Pro Ser Glu Arg Lys Leu Ile Ala Thr Ser Thr
        195                 200                 205

Thr Cys Trp Ser Ile Met Leu Ala Thr Leu Val Tyr Leu Ser Phe Leu
    210                 215                 220

Val Gly Pro Val Thr Val Leu Lys Val Tyr Gly Val Pro Tyr Ile Ile
225                 230                 235                 240

Phe Val Met Trp Leu Asp Ala Val Thr Tyr Leu His His His Gly His
                245                 250                 255

Asp Asp Lys Leu Pro Trp Tyr Arg Gly Lys Glu Trp Ser Tyr Leu Arg
            260                 265                 270

Gly Gly Leu Thr Thr Ile Asp Arg Asp Tyr Gly Ile Phe Asn Asn Ile
        275                 280                 285

His His Asp Ile Gly Thr His Val Ile His His Leu Phe Pro Gln Ile
    290                 295                 300

Pro His Tyr His Leu Val Asp Ala Thr Lys Ser Ala Lys His Val Leu
305                 310                 315                 320

Gly Arg Tyr Tyr Arg Glu Pro Lys Thr Ser Gly Ala Ile Pro Ile His
                325                 330                 335

Leu Val Glu Ser Leu Val Ala Ser Ile Lys Lys Asp His Tyr Val Ser
            340                 345                 350

Asp Thr Gly Asp Ile Val Phe Tyr Glu Thr Asp Pro Asp Leu Tyr Val
```

Tyr Ala Ser Asp Lys Ser Lys Ile Asn
        370             375

<210> SEQ ID NO 13
<211> LENGTH: 380
<212> TYPE: PRT
<213> ORGANISM: Glycine max

<400> SEQUENCE: 13

Met Val Lys Asp Thr Lys Pro Leu Ala Tyr Ala Asn Asn Gly Tyr
 1               5                  10                  15

Gln Gln Lys Gly Ser Ser Phe Asp Phe Asp Pro Ser Ala Pro Pro Pro
                20                  25                  30

Phe Lys Ile Ala Glu Ile Arg Ala Ser Ile Pro Lys His Cys Trp Val
            35                  40                  45

Lys Asn Pro Trp Arg Ser Leu Ser Tyr Val Leu Arg Asp Val Leu Val
    50                  55                  60

Ile Ala Ala Leu Val Ala Ala Ile His Phe Asp Asn Trp Leu Leu
65              70                  75                  80

Trp Leu Ile Tyr Cys Pro Ile Gln Gly Thr Met Phe Trp Ala Leu Phe
                85                  90                  95

Val Leu Gly His Asp Cys Gly His Gly Ser Phe Ser Asp Ser Pro Leu
            100                 105                 110

Leu Asn Ser Leu Val Gly His Ile Leu His Ser Ser Ile Leu Val Pro
        115                 120                 125

Tyr His Gly Trp Arg Ile Ser His Arg Thr His His Gln Asn His Gly
    130                 135                 140

His Ile Glu Lys Asp Glu Ser Trp Val Pro Leu Thr Glu Lys Ile Tyr
145                 150                 155                 160

Lys Asn Leu Asp Ser Met Thr Arg Leu Ile Arg Phe Thr Val Pro Phe
                165                 170                 175

Pro Leu Phe Val Tyr Pro Ile Tyr Leu Phe Ser Arg Ser Pro Gly Lys
            180                 185                 190

Glu Gly Ser His Phe Asn Pro Tyr Ser Asn Leu Phe Pro Pro Ser Glu
        195                 200                 205

Arg Lys Gly Ile Ala Ile Ser Thr Leu Cys Trp Ala Thr Met Phe Ser
    210                 215                 220

Leu Leu Ile Tyr Leu Ser Phe Ile Thr Ser Pro Leu Leu Val Leu Lys
225                 230                 235                 240

Leu Tyr Gly Ile Pro Tyr Trp Ile Phe Val Met Trp Leu Asp Phe Val
                245                 250                 255

Thr Tyr Leu His His His Gly His His Gln Lys Leu Pro Trp Tyr Arg
            260                 265                 270

Gly Lys Glu Trp Ser Tyr Leu Arg Gly Gly Leu Thr Thr Val Asp Arg
        275                 280                 285

Asp Tyr Gly Trp Ile Tyr Asn Ile His His Asp Ile Gly Thr His Val
    290                 295                 300

Ile His His Leu Phe Pro Gln Ile Pro His Tyr His Leu Val Glu Ala
305                 310                 315                 320

Thr Gln Ala Ala Lys Pro Val Leu Gly Asp Tyr Tyr Arg Glu Pro Glu
                325                 330                 335

Arg Ser Ala Pro Leu Pro Phe His Leu Ile Lys Tyr Leu Ile Gln Ser
            340                 345                 350

```
Met Arg Gln Asp His Phe Val Ser Asp Thr Gly Asp Val Val Tyr Tyr
        355                 360                 365

Gln Thr Asp Ser Leu Leu His Ser Gln Arg Asp
370                 375                 380

<210> SEQ ID NO 14
<211> LENGTH: 383
<212> TYPE: PRT
<213> ORGANISM: Arabidopsis thaliana

<400> SEQUENCE: 14

Met Gly Ala Gly Gly Arg Met Pro Val Pro Thr Ser Ser Lys Lys Ser
  1               5                  10                  15

Glu Thr Asp Thr Thr Lys Arg Val Pro Cys Glu Lys Pro Pro Phe Ser
             20                  25                  30

Val Gly Asp Leu Lys Lys Ala Ile Pro Pro His Cys Phe Lys Arg Ser
         35                  40                  45

Ile Pro Arg Ser Phe Ser Tyr Leu Ile Ser Asp Ile Ile Ala Ser
     50                  55                  60

Cys Phe Tyr Tyr Val Ala Thr Asn Tyr Phe Ser Leu Leu Pro Gln Pro
 65                  70                  75                  80

Leu Ser Tyr Leu Ala Trp Pro Leu Tyr Trp Ala Cys Gln Gly Cys Val
                 85                  90                  95

Leu Thr Gly Ile Trp Val Ile Ala His Glu Cys Gly His His Ala Phe
            100                 105                 110

Ser Asp Tyr Gln Trp Leu Asp Asp Thr Val Gly Leu Ile Phe His Ser
        115                 120                 125

Phe Leu Leu Val Pro Tyr Phe Ser Trp Lys Tyr Ser His Arg Arg His
    130                 135                 140

His Ser Asn Thr Gly Ser Leu Glu Arg Asp Glu Val Phe Val Pro Lys
145                 150                 155                 160

Gln Lys Ser Ala Ile Lys Trp Tyr Gly Lys Tyr Leu Asn Asn Pro Leu
                165                 170                 175

Gly Arg Ile Met Met Leu Thr Val Gln Phe Val Leu Gly Trp Pro Leu
            180                 185                 190

Tyr Leu Ala Phe Asn Val Ser Gly Arg Pro Tyr Asp Gly Phe Ala Cys
        195                 200                 205

His Phe Phe Pro Asn Ala Pro Ile Tyr Asn Asp Arg Glu Arg Leu Gln
    210                 215                 220

Ile Tyr Leu Ser Asp Ala Gly Ile Leu Ala Val Cys Phe Gly Leu Tyr
225                 230                 235                 240

Arg Tyr Ala Ala Ala Gln Gly Met Ala Ser Met Ile Cys Leu Tyr Gly
                245                 250                 255

Val Pro Leu Leu Ile Val Asn Ala Phe Leu Val Leu Ile Thr Tyr Leu
            260                 265                 270

Gln His Thr His Pro Ser Leu Pro His Tyr Asp Ser Ser Glu Trp Asp
        275                 280                 285

Trp Leu Arg Gly Ala Leu Ala Thr Val Asp Arg Asp Tyr Gly Ile Leu
    290                 295                 300

Asn Lys Val Phe His Asn Ile Thr Asp Thr His Val Ala His His Leu
305                 310                 315                 320

Phe Ser Thr Met Pro His Tyr Asn Ala Met Glu Ala Thr Lys Ala Ile
                325                 330                 335

Lys Pro Ile Leu Gly Asp Tyr Tyr Gln Phe Asp Gly Thr Pro Trp Tyr
            340                 345                 350
```

```
Val Ala Met Tyr Arg Glu Ala Lys Glu Cys Ile Tyr Val Glu Pro Asp
        355                 360                 365
Arg Glu Gly Asp Lys Lys Gly Val Tyr Trp Tyr Asn Asn Lys Leu
        370                 375                 380

<210> SEQ ID NO 15
<211> LENGTH: 383
<212> TYPE: PRT
<213> ORGANISM: Glycine max

<400> SEQUENCE: 15

Met Gly Ala Gly Gly Arg Thr Asp Val Pro Ala Asn Arg Lys Ser
 1               5                  10                  15

Glu Val Asp Pro Leu Lys Arg Val Pro Phe Glu Lys Pro Gln Phe Ser
                20                  25                  30

Leu Ser Gln Ile Lys Lys Ala Ile Pro Pro His Cys Phe Gln Arg Ser
            35                  40                  45

Val Leu Arg Ser Phe Ser Tyr Val Val Tyr Asp Leu Thr Ile Ala Phe
        50                  55                  60

Cys Leu Tyr Tyr Val Ala Thr His Tyr Phe His Leu Leu Pro Gly Pro
 65                  70                  75                  80

Leu Ser Phe Arg Gly Met Ala Ile Tyr Trp Ala Val Gln Gly Cys Ile
                85                  90                  95

Leu Thr Gly Val Trp Val Ile Ala His Glu Cys Gly His His Ala Phe
            100                 105                 110

Ser Asp Tyr Gln Leu Leu Asp Asp Ile Val Gly Leu Ile Leu His Ser
        115                 120                 125

Ala Leu Leu Val Pro Tyr Phe Ser Trp Lys Tyr Ser His Arg Arg His
130                 135                 140

His Ser Asn Thr Gly Ser Leu Glu Arg Asp Glu Val Phe Val Pro Lys
145                 150                 155                 160

Gln Lys Ser Cys Ile Lys Trp Tyr Ser Lys Tyr Leu Asn Asn Pro Pro
                165                 170                 175

Gly Arg Val Leu Thr Leu Ala Val Thr Leu Thr Leu Gly Trp Pro Leu
                180                 185                 190

Tyr Leu Ala Leu Asn Val Ser Gly Arg Pro Tyr Asp Arg Phe Ala Cys
            195                 200                 205

His Tyr Asp Pro Tyr Gly Pro Ile Tyr Ser Asp Arg Glu Arg Leu Gln
        210                 215                 220

Ile Tyr Ile Ser Asp Ala Gly Val Leu Ala Val Val Tyr Gly Leu Phe
225                 230                 235                 240

Arg Leu Ala Met Ala Lys Gly Leu Ala Trp Val Val Cys Val Tyr Gly
                245                 250                 255

Val Pro Leu Leu Val Val Asn Gly Phe Leu Val Leu Ile Thr Phe Leu
                260                 265                 270

Gln His Thr His Pro Ala Leu Pro His Tyr Thr Ser Ser Glu Trp Asp
            275                 280                 285

Trp Leu Arg Gly Ala Leu Ala Thr Val Asp Arg Asp Tyr Gly Ile Leu
        290                 295                 300

Asn Lys Val Phe His Asn Ile Thr Asp Thr His Val Ala His His Leu
305                 310                 315                 320

Phe Ser Thr Met Pro His Tyr His Ala Met Glu Ala Thr Lys Ala Ile
                325                 330                 335

Lys Pro Ile Leu Gly Glu Tyr Tyr Arg Phe Asp Glu Thr Pro Phe Val
```

```
                        340                 345                 350
Lys Ala Met Trp Arg Glu Ala Arg Glu Cys Ile Tyr Val Glu Pro Asp
                355                 360                 365
Gln Ser Thr Glu Ser Lys Gly Val Phe Trp Tyr Asn Asn Lys Leu
        370                 375                 380

<210> SEQ ID NO 16
<211> LENGTH: 383
<212> TYPE: PRT
<213> ORGANISM: Glycine max

<400> SEQUENCE: 16

Met Gly Ala Gly Gly Arg Met Ser Ala Pro Asn Gly Glu Thr Glu Val
  1               5                  10                  15
Lys Arg Asn Pro Leu Gln Lys Val Pro Thr Ser Lys Pro Pro Phe Thr
                 20                  25                  30
Val Gly Asp Ile Lys Lys Ala Ile Pro Pro His Cys Phe Gln Arg Ser
             35                  40                  45
Leu Ile Arg Ser Phe Ser Tyr Val Val Tyr Asp Leu Ile Leu Val Ser
         50                  55                  60
Ile Met Tyr Tyr Val Ala Asn Thr Tyr Phe His Leu Leu Pro Ser Pro
 65                  70                  75                  80
Tyr Cys Tyr Ile Ala Trp Pro Ile Tyr Trp Ile Cys Gln Gly Cys Val
                 85                  90                  95
Cys Thr Gly Ile Trp Val Asn Ala His Glu Cys Gly His His Ala Phe
                100                 105                 110
Ser Asp Tyr Gln Trp Val Asp Asp Thr Val Gly Leu Ile Leu His Ser
            115                 120                 125
Ala Leu Leu Val Pro Tyr Phe Ser Trp Lys Tyr Ser His Arg Arg His
        130                 135                 140
His Ser Asn Thr Gly Ser Leu Glu Arg Asp Glu Val Phe Val Pro Lys
145                 150                 155                 160
Pro Lys Ser Gln Leu Gly Trp Tyr Ser Lys Tyr Leu Asn Asn Pro Pro
                165                 170                 175
Gly Arg Val Leu Ser Leu Thr Ile Thr Leu Thr Leu Gly Trp Pro Leu
            180                 185                 190
Tyr Leu Ala Phe Asn Val Ser Gly Arg Pro Tyr Asp Arg Phe Ala Cys
        195                 200                 205
His Tyr Asp Pro Tyr Gly Pro Ile Tyr Asn Asn Arg Glu Arg Leu Gln
    210                 215                 220
Ile Phe Ile Ser Asp Ala Gly Val Leu Gly Val Cys Tyr Leu Leu Tyr
225                 230                 235                 240
Arg Ile Ala Leu Val Lys Gly Leu Ala Trp Leu Val Cys Val Tyr Gly
                245                 250                 255
Val Pro Leu Leu Val Val Asn Gly Phe Leu Val Leu Ile Thr Tyr Leu
            260                 265                 270
Gln His Thr His Pro Ser Leu Pro His Tyr Asp Ser Thr Glu Trp Asp
        275                 280                 285
Trp Leu Arg Gly Ala Leu Ala Thr Cys Asp Arg Asp Tyr Gly Val Leu
    290                 295                 300
Asn Lys Val Phe His Asn Ile Thr Asp Thr His Val Val His His Leu
305                 310                 315                 320
Phe Ser Thr Met Pro His Tyr Asn Ala Met Glu Ala Thr Lys Ala Val
                325                 330                 335
```

Lys Pro Leu Leu Gly Asp Tyr Tyr Gln Phe Asp Gly Thr Pro Ile Tyr
                340                 345                 350

Lys Glu Met Trp Arg Glu Ala Lys Glu Cys Leu Tyr Val Glu Lys Asp
            355                 360                 365

Glu Ser Ser Gln Gly Lys Gly Val Phe Trp Tyr Lys Asn Lys Leu
    370                 375                 380

<210> SEQ ID NO 17
<211> LENGTH: 387
<212> TYPE: PRT
<213> ORGANISM: S. commersonii

<400> SEQUENCE: 17

Met Gly Leu Ala Lys Glu Thr Thr Met Gly Gly Arg Gly Arg Val Ala
  1               5                  10                  15

Lys Val Glu Val Gln Gly Lys Lys Pro Leu Ser Arg Val Pro Asn Thr
               20                  25                  30

Lys Pro Pro Phe Thr Val Gly Gln Leu Lys Lys Ala Ile Pro Pro His
            35                  40                  45

Cys Phe Gln Arg Ser Leu Leu Thr Ser Phe Ser Tyr Val Val Tyr Asp
        50                  55                  60

Leu Ser Phe Ala Phe Ile Phe Tyr Ile Ala Thr Thr Tyr Phe His Leu
 65                  70                  75                  80

Leu Pro Gln Pro Phe Ser Leu Ile Ala Trp Pro Ile Tyr Trp Val Leu
                 85                  90                  95

Gln Gly Cys Leu Leu Thr Gly Val Trp Val Ile Ala His Glu Cys Gly
                100                 105                 110

His His Ala Phe Ser Lys Tyr Gln Trp Val Asp Asp Val Val Gly Leu
            115                 120                 125

Thr Leu His Ser Thr Leu Leu Val Pro Tyr Phe Ser Trp Lys Ile Ser
        130                 135                 140

His Arg Arg His His Ser Asn Thr Gly Ser Leu Asp Arg Asp Glu Val
145                 150                 155                 160

Phe Val Pro Lys Pro Lys Ser Lys Val Ala Trp Phe Ser Lys Tyr Leu
                165                 170                 175

Asn Asn Pro Leu Gly Arg Ala Val Ser Leu Leu Val Thr Leu Thr Ile
                180                 185                 190

Gly Trp Pro Met Tyr Leu Ala Phe Asn Val Ser Gly Arg Pro Tyr Asp
            195                 200                 205

Ser Phe Ala Ser His Tyr His Pro Tyr Ala Pro Ile Tyr Ser Asn Arg
        210                 215                 220

Glu Arg Leu Leu Ile Tyr Val Ser Asp Val Ala Leu Phe Ser Val Thr
225                 230                 235                 240

Tyr Ser Leu Tyr Arg Val Ala Thr Leu Lys Gly Leu Val Trp Leu Leu
                245                 250                 255

Cys Val Tyr Gly Val Pro Leu Leu Ile Val Asn Gly Phe Leu Val Thr
                260                 265                 270

Ile Thr Tyr Leu Gln His Thr His Phe Ala Leu Pro His Tyr Asp Ser
            275                 280                 285

Ser Glu Trp Asp Trp Leu Lys Gly Ala Leu Ala Thr Met Asp Arg Asp
        290                 295                 300

Tyr Gly Ile Leu Asn Lys Val Phe His His Ile Thr Asp Thr His Val
305                 310                 315                 320

Ala His His Leu Phe Ser Thr Met Pro His Tyr His Ala Met Glu Ala
                325                 330                 335

```
Thr Asn Ala Ile Lys Pro Ile Leu Gly Glu Tyr Tyr Gln Phe Asp Asp
            340                 345                 350

Thr Pro Phe Tyr Lys Ala Leu Trp Arg Glu Ala Arg Glu Cys Leu Tyr
            355                 360                 365

Val Glu Pro Asp Glu Gly Thr Ser Glu Lys Gly Val Tyr Trp Tyr Arg
        370                 375                 380

Asn Lys Tyr
385

<210> SEQ ID NO 18
<211> LENGTH: 387
<212> TYPE: PRT
<213> ORGANISM: Ricinus communis

<400> SEQUENCE: 18

Met Gly Gly Gly Arg Met Ser Thr Val Ile Thr Ser Asn Asn Ser
 1               5                  10                  15

Glu Lys Lys Gly Gly Ser Ser His Leu Lys Arg Ala Pro His Thr Lys
                20                  25                  30

Pro Pro Phe Thr Leu Gly Asp Leu Lys Arg Ala Ile Pro Pro His Cys
            35                  40                  45

Phe Glu Arg Ser Phe Val Arg Ser Phe Ser Tyr Val Ala Tyr Asp Val
        50                  55                  60

Cys Leu Ser Phe Leu Phe Tyr Ser Ile Ala Thr Asn Phe Phe Pro Tyr
 65                  70                  75                  80

Ile Ser Ser Pro Leu Ser Tyr Val Ala Trp Leu Val Tyr Trp Leu Phe
                85                  90                  95

Gln Gly Cys Ile Leu Thr Gly Leu Trp Val Ile Gly His Glu Cys Gly
            100                 105                 110

His His Ala Phe Ser Glu Tyr Gln Leu Ala Asp Asp Ile Val Gly Leu
        115                 120                 125

Ile Val His Ser Ala Leu Leu Val Pro Tyr Phe Ser Trp Lys Tyr Ser
130                 135                 140

His Arg Arg His His Ser Asn Ile Gly Ser Leu Glu Arg Asp Glu Val
145                 150                 155                 160

Phe Val Pro Lys Ser Lys Ser Lys Ile Ser Trp Tyr Ser Lys Tyr Ser
                165                 170                 175

Asn Asn Pro Pro Gly Arg Val Leu Thr Leu Ala Ala Thr Leu Leu Leu
            180                 185                 190

Gly Trp Pro Leu Tyr Leu Ala Phe Asn Val Ser Gly Arg Pro Tyr Asp
        195                 200                 205

Arg Phe Ala Cys His Tyr Asp Pro Tyr Gly Pro Ile Phe Ser Glu Arg
    210                 215                 220

Glu Arg Leu Gln Ile Tyr Ile Ala Asp Leu Gly Ile Phe Ala Thr Thr
225                 230                 235                 240

Phe Val Leu Tyr Gln Ala Thr Met Ala Lys Gly Leu Ala Trp Val Met
                245                 250                 255

Arg Ile Tyr Gly Val Pro Leu Leu Ile Val Asn Cys Phe Leu Val Met
            260                 265                 270

Ile Thr Tyr Leu Gln His Thr His Pro Ala Ile Pro Arg Tyr Gly Ser
        275                 280                 285

Ser Glu Trp Asp Trp Leu Arg Gly Ala Met Val Thr Val Asp Arg Asp
    290                 295                 300

Tyr Gly Val Leu Asn Lys Val Phe His Asn Ile Ala Asp Thr His Val
```

```
                305                 310                 315                 320
Ala His His Leu Phe Ala Thr Val Pro His Tyr His Ala Met Glu Ala
                    325                 330                 335

Thr Lys Ala Ile Lys Pro Ile Met Gly Glu Tyr Tyr Arg Tyr Asp Gly
            340                 345                 350

Thr Pro Phe Tyr Lys Ala Leu Trp Arg Glu Ala Lys Glu Cys Leu Phe
        355                 360                 365

Val Glu Pro Asp Glu Gly Ala Pro Thr Gln Gly Val Phe Trp Tyr Arg
    370                 375                 380

Asn Lys Tyr
385

<210> SEQ ID NO 19
<211> LENGTH: 18
<212> TYPE: DNA
<213> ORGANISM: Unknown
<220> FEATURE:
<223> OTHER INFORMATION: Description of Unknown Organism: unknown
<223> OTHER INFORMATION: n at positions 3, 9, and 15 refers to any of
      the four bases (nucleotides) A, C, G or T

<400> SEQUENCE: 19
gsncaygant gygsncay                                                        18

<210> SEQ ID NO 20
<211> LENGTH: 20
<212> TYPE: DNA
<213> ORGANISM: Unknown
<220> FEATURE:
<223> OTHER INFORMATION: Description of Unknown Organism: unknown
<223> OTHER INFORMATION: n at positions 3, 12, and 15 refers to any of
      the four bases (nucleotides) A, C, G or T

<400> SEQUENCE: 20
ranadrtgrt gnrbnayrtg                                                      20

<210> SEQ ID NO 21
<211> LENGTH: 20
<212> TYPE: DNA
<213> ORGANISM: Unknown
<220> FEATURE:
<223> OTHER INFORMATION: Description of Unknown Organism: unknown
<223> OTHER INFORMATION: n at position 6 refers to any of the four bases
      (nucleotides) A, C, G or T

<400> SEQUENCE: 21
tggmgnttya arcaygaymg                                                      20

<210> SEQ ID NO 22
<211> LENGTH: 20
<212> TYPE: DNA
<213> ORGANISM: Unknown
<220> FEATURE:
<223> OTHER INFORMATION: Description of Unknown Organism: unknown
<223> OTHER INFORMATION: n at position 3 refers to any of the four bases
      (nucleotides) A, C, G or T

<400> SEQUENCE: 22
gtnswcatcc araartgrta                                                      20

<210> SEQ ID NO 23
<211> LENGTH: 20
<212> TYPE: DNA
<213> ORGANISM: Unknown
<220> FEATURE:
```

```
<223> OTHER INFORMATION: Description of Unknown Organism: unknown
<223> OTHER INFORMATION: n at position 12 refers to any of the four
      bases (nucleotides) A, C, G or T

<400> SEQUENCE: 23
caygartgyg gncaycaygc                                              20

<210> SEQ ID NO 24
<211> LENGTH: 20
<212> TYPE: DNA
<213> ORGANISM: Unknown
<220> FEATURE:
<223> OTHER INFORMATION: Description of Unknown Organism: unknown
<223> OTHER INFORMATION: n at positions 3 and 6 refers to any of the
      four bases (nucleotides) A, C, G or T

<400> SEQUENCE: 24
ccncknarcc artcccaytc                                              20

<210> SEQ ID NO 25
<211> LENGTH: 20
<212> TYPE: DNA
<213> ORGANISM: Unknown
<220> FEATURE:
<223> OTHER INFORMATION: Description of Unknown Organism: unknown
<223> OTHER INFORMATION: n at position 3 refers to any of the four bases
      (nucleotides) A, C, G or T

<400> SEQUENCE: 25
acncaycayc araaycaygg                                              20

<210> SEQ ID NO 26
<211> LENGTH: 20
<212> TYPE: DNA
<213> ORGANISM: Unknown
<220> FEATURE:
<223> OTHER INFORMATION: Description of Unknown Organism: unknown
<223> OTHER INFORMATION: n at positions 9 and 12 refers to any of the
      four bases (nucleotides) A, C, G or T

<400> SEQUENCE: 26
caytgyttnc cnckrtacca                                              20
```